US008809386B2

(12) United States Patent
Robinson et al.

(10) Patent No.: US 8,809,386 B2
(45) Date of Patent: Aug. 19, 2014

(54) USE OF DYNAMIN RING STABILIZERS

(75) Inventors: Phillip J. Robinson, North Rocks (AU); Sanja Sever, Brookline, MA (US)

(73) Assignees: Children's Medical Research Institute, Westmead, NSW (AU); The General Hospital Corporation, Boston, MA (US)

( * ) Notice: Subject to any disclaimer, the term of this patent is extended or adjusted under 35 U.S.C. 154(b) by 0 days.

(21) Appl. No.: 13/321,415

(22) PCT Filed: May 21, 2010

(86) PCT No.: PCT/AU2010/000677
§ 371 (c)(1),
(2), (4) Date: Jan. 25, 2012

(87) PCT Pub. No.: WO2010/132959
PCT Pub. Date: Nov. 25, 2010

(65) Prior Publication Data
US 2012/0122968 A1 May 17, 2012

Related U.S. Application Data

(60) Provisional application No. 61/180,261, filed on May 21, 2009.

(51) Int. Cl.
*A61K 31/35* (2006.01)
(52) U.S. Cl.
USPC ...................................................... 514/456
(58) Field of Classification Search
USPC ...................................................... 514/456
See application file for complete search history.

(56) References Cited

U.S. PATENT DOCUMENTS

2007/0197438 A1 8/2007 Reiser et al.
2010/0272709 A1 10/2010 Reiser et al.

FOREIGN PATENT DOCUMENTS

WO 95/14464 A1 6/1995
WO 01/64880 A3 9/2001
WO 2005/049009 A1 6/2005
WO 2007/056435 A2 5/2007
WO 2009/034464 A2 3/2009

OTHER PUBLICATIONS

International Search Report, form PCT/ISA/210 (second sheet), PCT/AU2010/000677, date of completion: Jul. 14, 2010; date of mailing: Jul. 20, 2010, three (3) pages.
European Search Report dated Nov. 21, 2012 and Search Opinion dated Dec. 3, 2012 for EP 10777248.5, five (5) pages.
Examiner's report (English translation) dated Nov. 29, 2012 issued in relation to CN 201080033320.7, five (5) pages.

Abban, C.A. et al., "HPV16 and BPV1 Infection Can Be Blocked by the Dynamin Inhibitor Dynasore," American Journal of Therapeutics, Oct. 1, 2008 (author transcript available in PMC), vol. 15, No. 4, pp. 304-311.
Chao, W-T. et al., "Focal Adhesion Disassembly Requires Clathrin-Dependent Endocytosis of Integrins," FEBS Letters 583, Mar. 22, 2009 (available online), pp. 1337-1343, © 2009 Federation of European Biochemical Societies, published by Elsevier B.V.
Copelovitch, L. et al., "Hypothesis: Dent Disease is an Under-recognized Cause of Focal Glomerulosclerosis," Clinical Journal of the American Society of Nephrology, May 7, 2007 (accepted), vol. 2, pp. 914-918, © 2007 by the American Society of Nephrology.
Faul, C. et al., "Actin Up: Regulation of Podocyte Structure and Function by Components of the Actin Cytoskeleton," Trends in Cell Biology, Sep. 4, 2007 (available online), vol. 17, No. 9, pp. 428-437, © 2007 Elsevier Ltd.
Gazit, A. et al., "Tyrphostins I: Synthesis and Biological Activity of Protein Tyrosine Kinase Inhibitors," Journal of Medicinal Chemistry, vol. 32, No. 10, pp. 2344-2352, © 1989 American Chemical Society.
Gazit, A. et al. "Tyrphostins 2. Heterocyclic and α-Substituted Benzylidenomalononitrile Tyrphostins as Potent Inhibitors of EGF Receptor and ErbB2/neu Tyrosine Kinases," Journal of Medicinal Chemistry, (1991), vol. 34, No. 6, pp. 1896-1907, © 1991 American Chemical Society.
Gazit, A. et al., "Tyrphostins 3: Structure-Activity Relationship Studies of α-Substituted Benzylidenemalonitrile 5-S-Aryltyrphostins," Journal of Medicinal Chemistry, vol. 36, No. 23, pp. 3556-3564, © 1993 American Chemical Society.
Gazit, A. et al., "Tyrphostins 5. Potent Inhibitors of Platelet-Derived Growth Factor Receptor Tyrosine Kinase: Structure-Activity Relationships in Quinoxalines, Quinolines and Indole Tyrphostins," Journal of Medicinal Chemistry, vol. 39, No. 11, pp. 2170-2177, © 1996 American Chemical Society.
Gazit, A. et al., "Tyrphostins 6. Dimeric Benzylidenemalononitrile Tyrphostins: Potent Inhibitors of EGF Receptor Tyrosine Kinase In Vitro," Journal of Medicinal Chemistry, vol. 39, No. 25, pp. 4905-4911, © 1996 American Chemical Society.

(Continued)

*Primary Examiner* — Kevin E Weddington
(74) *Attorney, Agent, or Firm* — Rothwell, Figg, Ernst & Manbeck P.C.

(57) ABSTRACT

There is provided a method for promoting dynamin ring formation and/or maintenance of dynamin rings in a cell, comprising treating the cell with an effective amount of a dynamin ring stabilizer, or a prodrug or pharmaceutically acceptable salt of the dynamin ring stabilizer. The maintenance or accumulation of dynamin ring formation has particular application in the prophylaxis or treatment of a kidney disease or condition characterized by proteinuria. A dynamin ring stabilizer can be any agent that interacts with dynamin to promote dynamin ring assembly and/or inhibit dynamin ring disassembly. There are also provided methods for prophylaxis or treatment of podocyte dysfunction and/or maintaining or inducing actin cytoskeleton formation in a cell utilizing dynamin ring stabilizers, and for screening a test agent for use as a dynamin ring stabilizer.

17 Claims, 13 Drawing Sheets

(56) References Cited

OTHER PUBLICATIONS

Gu, C. et al., "Direct Dynamin-Actin Interactions Regulate the Actin Cytoskeleton," The EMBO Journal, vol. 29, No. 21, pp. 3593-3606, © 2010 European Molecular Biology Organization.

Henderson, J.M. et al.., "Mice With Altered α-Actinin-4 Expression Have Distinct Morphologic Patterns of Glomerular Disease," Kidney International, Jan. 9, 2008 (published online), vol. 73, No. 6, pp. 741-750, © 2008 International Society of Nephrology.

Hill, T.A. et al., "Long Chain Amines and Long Chain Ammonium Salts as Novel Inhibitors of Dynamin GTPase Activity.," Bioorganic & Medicinal Chemistry Letters, Mar. 29, 2004 (accepted), vol. 14, pp. 3275-3278, © 2004 Elsevier Ltd.

Hill, T. et al., "Small Molecule Inhibitors of Dynamin I GTPase Activity: Development of Dimeric Tyrphostins," Journal of Medicinal Chemistry, Oct. 29, 2005 (published on Web), vol. 48, No. 24, pp. 7781-7788, © 2005 American Chemical Society.

Hill, T.A. et al., "Inhibition of Dynamin Mediated Endocytosis by the Dynoles—Synthesis and Functional Activity of a Family of Indoles," Journal of Medicinal Chemistry, May 21, 2009 (published online), vol. 52, No. 12, pp. 3762-3773, © 2009 American Chemical Society.

Hill, T.A. et al., "Iminochromene Inhibitors of Dynamins I and II GTPase Activity and Endocytosis," Journal of Medicinal Chemistry, Apr. 28, 2010 (published online), vol. 53, No. 10, pp. 4094-4102, © 2010 American Chemical Society.

Hinshaw, J.E. et al., "Dynamin Self-Assembles Into Rings Suggesting a Mechanism for Coated Vesicle Budding," Nature, Mar. 9, 1995, vol. 374, pp. 190-192.

Kaplan, J.M. et al., "Mutations in ACTN4, Encoding α-Actinin-4, Cause Familial Focal Segmental Glomerulosclerosis," Nature Genetics, Mar. 2000, vol. 24, pp. 251-256, © 2000 Nature America Inc.

Levitzki, A. et al., "Tyrphostins as Molecular Tools and Potential Antiproliferative Drugs," TiPS, May 1991, vol. 12, pp. 171-174, © 1991 Elsevier Science Publications Ltd.

Lima, L.M. et al., "Bioisosterism: A Useful Strategy for Molecular Modification and Drug Design," Current Medicinal Chemistry, (2005), vol. 12, No. 1, pp. 23-49, © 2005 Bentham Science Publishers Ltd.

Macia, E. et al., "Dynasore, a Cell-Permeable Inhibitor of Dynamin," Developmental Cell 10, Jun. 2006, pp. 839-850, © 2006 Elsevier Inc.

Mazumder, A. et al., "Effects of Tyrphostins, Protein Kinase Inhibitors, on Human Immunodeficiency Virus Type I Integrase," Biochemistry, vol. 34, No. 46, pp. 15111-15122, © 1995 American Chemical Society.

Mundel, P. et al., "Rearrangements of the Cytoskeleton and Cell Contacts Induce Process Formation During Differentiation of Conditionally Immortalized Mouse Podocyte Cell Lines," Experimental Cell Research, vol. 236, No. EX973739, pp. 248-258, © 1997 by Academic Press.

Nankoe, S.R. et al., "Dynasore Puts a New Spin on Dynamin: A Surprising Dual Role During Vesicle Formation," Trends in Cell Biology, Oct. 24, 2006, vol. 16, No. 12, © Elsevier Ltd.

Odell, L.R. et al., "Azido and Diazarinyl Analogues of Bis-Tyrphostin as Asymmentrical Inhibitors of Dynamin GTPase," ChemMedChem, May 12, 2009 (published online), vol. 4, pp. 1182-1188, © 2009 Wiley-VCH Verlag GmbH & Co.

Orth, J.D. et al., "Dynamin at the Actin-Membrane Interface," Current Opinion in Cell Biology, (2003), vol. 15, pp. 31-39.

Otsuka, A. et al., "Dynamin 2 is Required for Actin Assembly in Phagocytosis in Sertoli Cells," Biochemical and Biophysical Research Communications, (2009) (Nov. 24, 2008 available online), vol. 378, pp. 478-482, © 2008 Elsevier Inc.

Quan, A. et al., "Myristyl Trimethyl Ammonium Bromide and Octadecyl Trimethyl Ammonium Bromide are Surface-Active Dynamin Inhibitors That Block Endocytosis Mediated by Dynamin I or Dynamin II," Molecular Pharmacology, Aug. 16, 2007 (accepted), vol. 72., No. 6, pp. 1425-1439, © 2007 The American Society for Pharmacology and Experimental Therapeutics.

Schafer, D.A., "Regulating Actin Dynamics at Membranes: A Focus on Dynamin," Traffic, Mar. 20, 2004 (accepted for publication), No. 5, pp. 463-469, © Blackwell Munksgaard 2004.

Sever, S. et al., "Proteolytic Processing of Dynamin by Cytoplasmic Cathepsin L is a Mechanism for Proteinuric Kidney Disease," The Journal of Clinical Investigation, Aug. 2007, vol. 117, No. 8, pp. 2095-2104.

Stowell, M.H.B. et al., "Nucleotide-Dependent Conformational Changes in Dynamin: Evidence for a Mechanochemical Molecular Spring," Nature Cell Biology, May 1999, vol. 1, pp. 27-32, © 1999 Macmillan Magazines Ltd.

Warnock, D.E. et al., "Dynamin Self-Assembly Stimulates Its GTPase Activity," The Journal of Biological Chemistry, (1996), Issue of Sep. 13, vol. 271, No. 37, pp. 22310-22314, © by The American Society for Biochemistry and Molecular Biology, Inc.

Welsh, G.I. et al., "The Podocyte Cytoskeleton—Key to a Functioning Glomerulus in Health and Disease," Nature Reviews/Nephrology, Jan. 2012, vol. 8, pp. 14-21, © 2011 Macmillan Publishers Limited.

Yamada, H. et al., "Dynasore, a Dynamin Inhibitor, Suppresses Lamellipodia Formation and Cancer Cell Invasion by Destabilizing Actin Filaments," Biochemical and Biophysical Research Communications, Oct. 24, 2009 (available online), vol. 390, pp. 1142-1148, © 2009 Elsevier Inc.

Yao, J. et al., "Alpha-Actinin-4 Mediated FSGS: An Inherited Kidney Disease Caused by an Aggregated and Rapidly Degraded Cytoskeletal Protein," PLoS Biology, Jun. 2004, vol. 2, No. 6, pp. 0787-0794, © 2004 Yao et al.

Zhang, J. et al., "From Spanish Fly to Room-Temperature Ionic Liquids (RTILs): Synthesis, Thermal Stability and Inhibition of Dynamin 1 GTPase by a Novel Class of RTILs," New Journal of Chemistry, Jan. 2008, vol. 32, pp. 28-36 (and cover page), 10 pages.

Zhang, P. et al., "Three-Dimensional Reconstruction of Dynamin in the Constricted State," Nature Cell Biology, Oct. 2001, vol. 3, pp. 922-926 (and supplemental information page), © 2001 Macmillan Magazines Ltd., 6 pages.

Massachusetts General Hospital Press Release, Aug. 1, 2007, "Molecular Mechanism of Common Forms of Kidney Disease Identified. Enzyme Causes Protein to Leak From Blood Into Urine, Changes to Target May Restore Kidney Function," 2 pages.

Asanuma K., Kim K., Oh J., Giardino L., Chabanis S., Faul C., Reiser J. and Mundel P. (2005) Synaptopodin regulates the actin-bundling activity of alpha-actinin in an isoform-specific manner. J. Clin. Invest. 115, 1188-1198.

Asanuma K., Yanagida-Asanuma E., Faul C., Tomino Y., Kim K. and Mundel P. (2006) Synaptopodin orchestrates actin organization and cell motility via regulation of RhoA signalling. Nat. Cell Biol. 8, 485-491.

Chappie J. S., Acharya S., Liu Y. W., Leonard M., Pucadyil T. J. and Schmid S. L. (2009) An intramolecular signaling element that modulates dynamin function in vitro and in vivo. Mol. Biol. Cell 20, 3561-3571.

Chen Y. J., Zhang P., Egelman E. H. and Hinshaw J. E. (2004) The stalk region of dynamin drives the constriction of dynamin tubes. Nat. Struct. Mol. Biol. 11, 574-575.

Cousin M. A. and Robinson P. J. (2001) The dephosphins: Dephosphorylation by calcineurin triggers synaptic vesicle endocytosis. Trends Neurosci. 24, 659-665.

Ichimura K., Kurihara H. and Sakai T. (2003) Actin filament organization of foot processes in rat podocytes. J. Histochem. Cytochem. 51, 1589-1600.

Jones N., Blasutig I. M., Eremina V., Ruston J. M., Bladt F., Li H., Huang H., Larose L., Li S. S., Takano T., Quaggin S. E. and Pawson T. (2006) Nck adaptor proteins link nephrin to the actin cytoskeleton of kidney podocytes. Nature 440, 818-823.

Moeller M. J., Soofi A., Braun G. S., Li X., Watzl C., Kriz W. and Holzman L. B. (2004) Protocadherin FAT1 binds Ena/VASP proteins and is necessary for actin dynamics and cell polarization. EMBO J. 23, 3769-3779.

Muhlberg A. B., Warnock D. E. and Schmid S. L. (1997) Domain structure and intramolecular regulation of dynamin GTPase. EMBO J. 16, 6676-6683.

(56) References Cited

OTHER PUBLICATIONS

Quan A. and Robinson P. J. (2005) Rapid purification of native dynamin I and colorimetric GTPase assay. Methods Enzymol. 404 (Ch 49), 556-569.

Reiser J., Oh J., Shirato I., Asanuma K., Hug A., Mundel T. M., Honey K., Ishidoh K., Kominami E., Kreidberg J. A., Tomino Y. and Mundel P. (2004) Podocyte migration during nephrotic syndrome requires a coordinated interplay between cathepsin L and alpha3 integrin. J. Biol. Chem. 279, 34827-34832.

Roux A., Uyhazi K., Frost A. and De Camilli P. (2006) GTP-dependent twisting of dynamin implicates constriction and tension in membrane fission. Nature 441, 528-531.

Saleem M. A., O'Hare M. J., Reiser J., Coward R. J., Inward C. D., Farren T., Xing C. Y., Ni L., Mathieson P. W. and Mundel P. (2002) A conditionally immortalized human podocyte cell line demonstrating nephrin and podocin expression. J Am Soc Nephrol 13, 630-638.

Sever S., Damke H. and Schmid S. L. (2000a) Dynamin:GTP controls the formation of constricted coated pits, the rate limiting step in clathrin-mediated endocytosis. J. Cell Biol. 150, 1137-1147.

Sever S., Damke H. and Schmid S. L. (2000b) Garrotes, springs, ratchets, and whips: Putting dynamin models to the test. Traffic 1, 385-392.

Sever S., Muhlberg A. B. and Schmid S. L. (1999) Impairment of dynamin's GAP domain stimulates receptor-mediated endocytosis. Nature 398, 481-486.

Sever S., Skoch J., Newmyer S., Ramachandran R., Ko D., McKee M., Bouley R., Ausiello D., Hyman B. T. and Bacskai B. J. (2006) Physical and functional connection between auxilin and dynamin during endocytosis. EMBO J. 25, 4163-4174.

Song B. D., Leonard M. and Schmid S. L. (2004) Dynamin GTPase domain mutants that differentially affect GTP binding, GTP hydrolysis and clathrin-mediated endocytosis. J. Biol. Chem. 279, 40431-40436.

Susztak K. and Bottinger E. P. (2006) Diabetic nephropathy: a frontier for personalized medicine. J Am Soc Nephrol 17, 361-367.

Tryggvason K., Patrakka J. and Wartiovaara J. (2006) Hereditary proteinuria syndromes and mechanisms of proteinuria. N. Engl. J. Med. 354, 1387-1401.

Van T. M., Dewitte D., Goethals M., Carlier M. F., Vandekerckhove J. and Ampe C. (1996) The actin binding site of thymosin beta 4 mapped by mutational analysis. EMBO J. 15, 201-210.

Weins A., Kenlan P., Herbert S., Le T. C., Villegas I., Kaplan B. S., Appel G. B. and Pollak M. R. (2005) Mutational and biological analysis of alpha-actinin-4 in focal segmental glomerulosclerosis. J Am Soc Nephrol 16, 3694-3701.

Dent Disease—GeneReviewsTM—NCBI Bookshelf. A service of the National Library of Medicine, National Institutes of Health. Authors—Lieske, J. C., et al. Pagon R.A et al—Editors. Gene ReviewsTM [Internet]. Seattle (WA) University of Washington, Seattle; 1993-2014. http://www.ncbi.nlm.nih.gov/books/NBK99494/. Published on-line Aug. 9, 2012.

Dent disease, Genetics Home Reference, U.S National Library of Medicine, http://ghr.nlm.nih.gov/condition/dent-disease. Published on-line Jun. 17, 2013.

CLCN5 chloride channel, Genetics Home Reference, U.S National Library of Medicine, http://ghr.nlm.nih.gov/gene/CLCN5. Published on-line Jun. 17, 2013.

OCRL—oculocerebrorenal syndrome of Lowe, Genetics Home Reference, U.S National Library of Medicine, http://ghr.nlm.nih.gov/gene/OCRL. Published on-line Jun. 17, 2013.

FIGURE 9
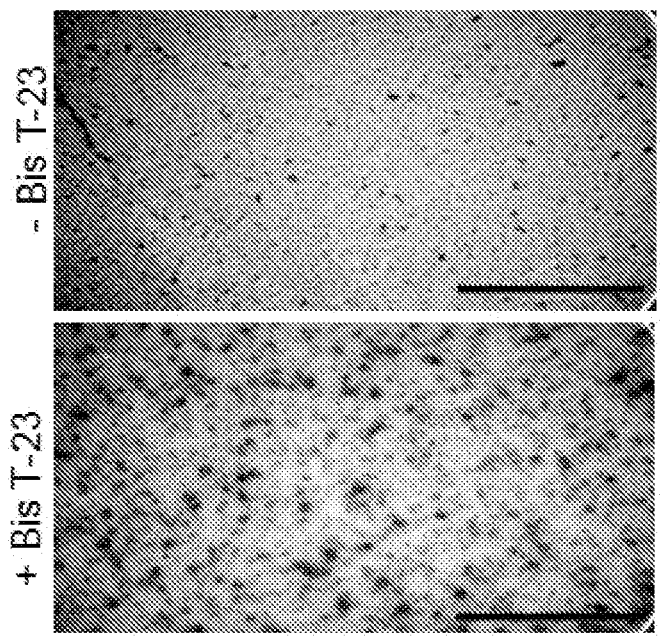
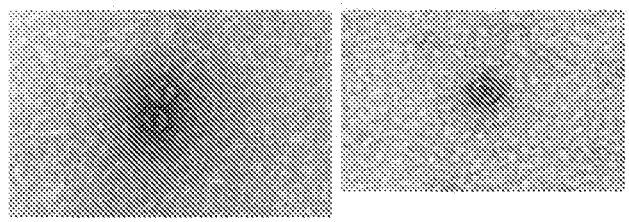
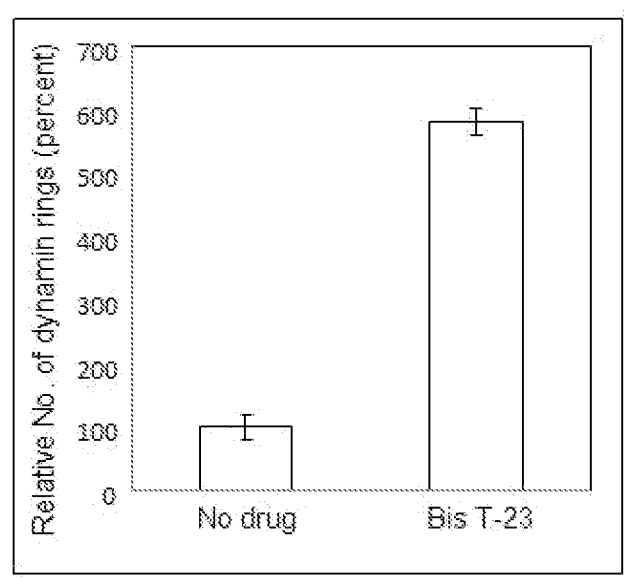

FIGURE 10
10A
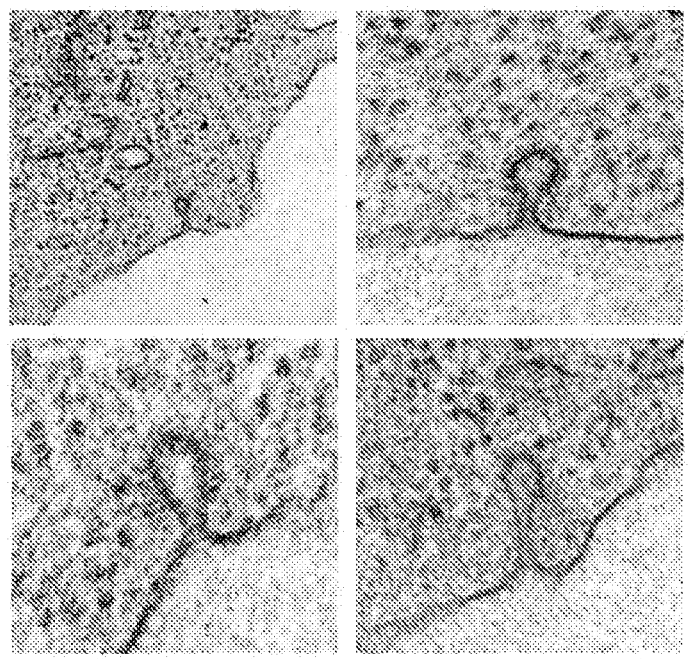
10B
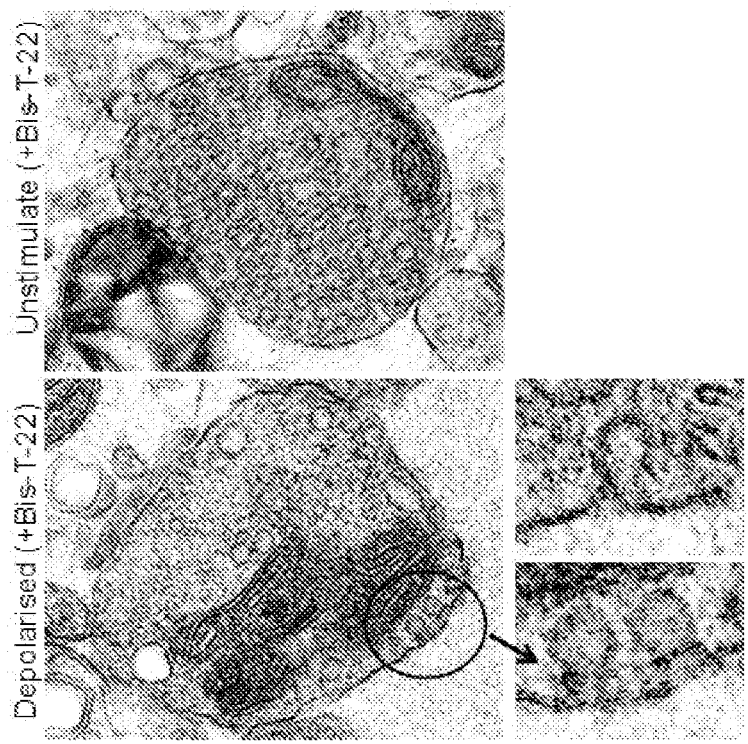

FIGURE 11
A
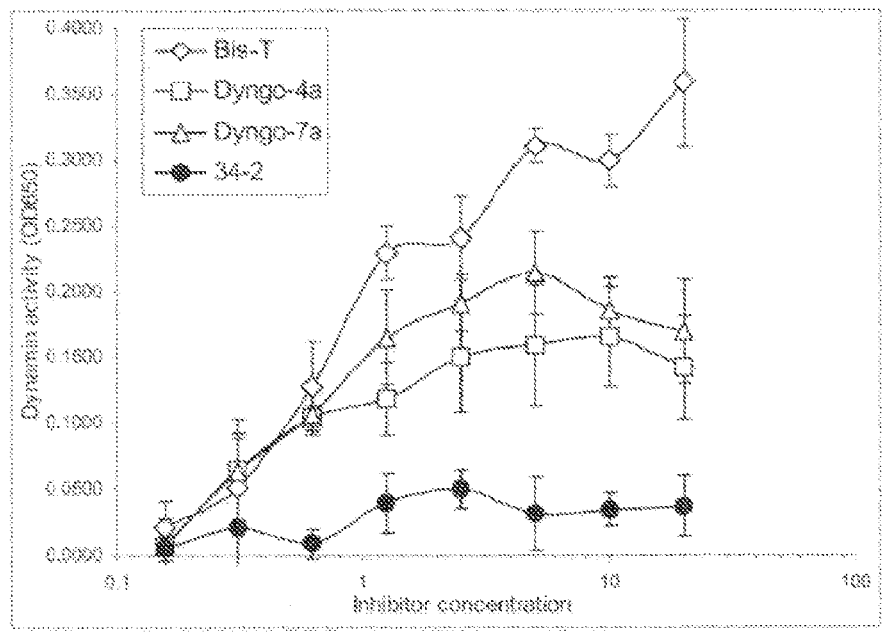
B
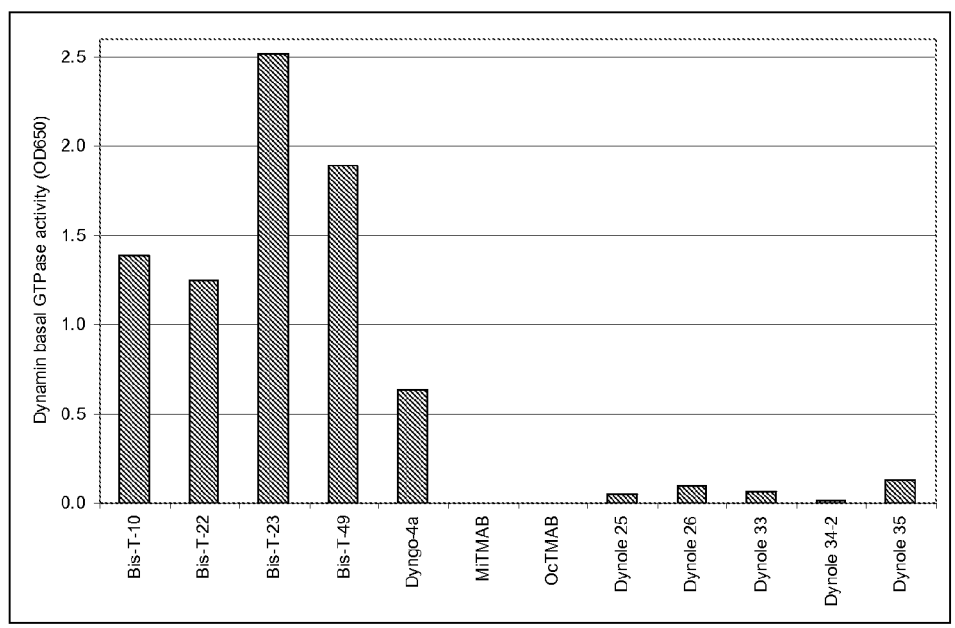

FIGURE 12

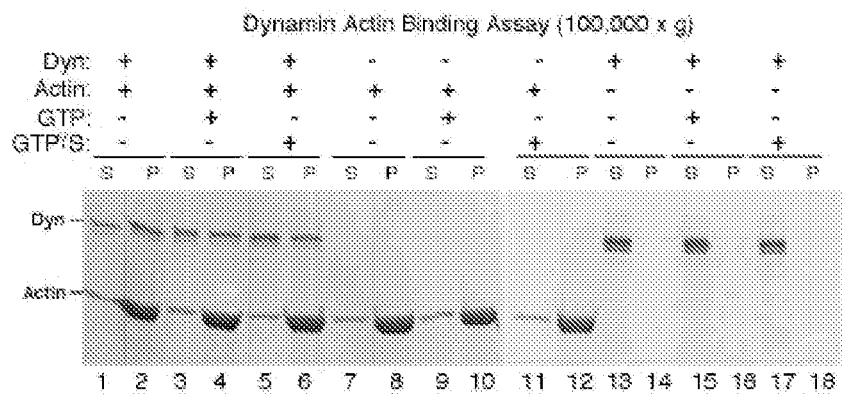

FIGURE 13

```
Dyn2a   399 RTGLFTPDLAFEAIVKKQVVKLKEPCLKCVDLVIQELISTVRQCTS 444
Dyn2b   399 RTGLFTPDMAFEAIVKKQLVKLKEPSLKCVDLVVSELATVIKKCAE 444
Dyn1a   399 RTGLFTPDLAFEATVKKQVQKLKEPSIKCVDMVVSELTSTIRKCSE 444
Dyn1b   399 RTGLFTPDMAFETIVKKQVKKIREPCLKCVDMVISELISTVRQCTK 444
Shi     394 RVGLFTPDMAFEAIVKRQIALLKEPVIKCVDLVVQELSVVVRMCTA 439
Cele    401 RVGLFTPDMAFEAIAKKQITRLKEPSLKCVDLVVNELANVIRQCAD 491
Vps1    438 APSLFVGIEAFEVLVKQQIRRFEEPSLRLVTLVFDELVRMLKQIIS 483
Dnm1    438 RPTLFVPELAFDLLVKPQIKLLLEPSQRCVELVYEELMKICHKCGS 483

DynK/K:     RTGLFTPDLAFEAIV  QVV L EPCL CVDLVIQELISTVRQCTS
DynK/A:     RTGLFTPDLAFEAIV  QVV L EPCL CVDLVIQELISTVRQCTS
DynE/K:     RTGLFTPDLAFEAIVKKQVVKLK PCLKCVDLVIQ LISTVRQCTS
```

FIGURE 14

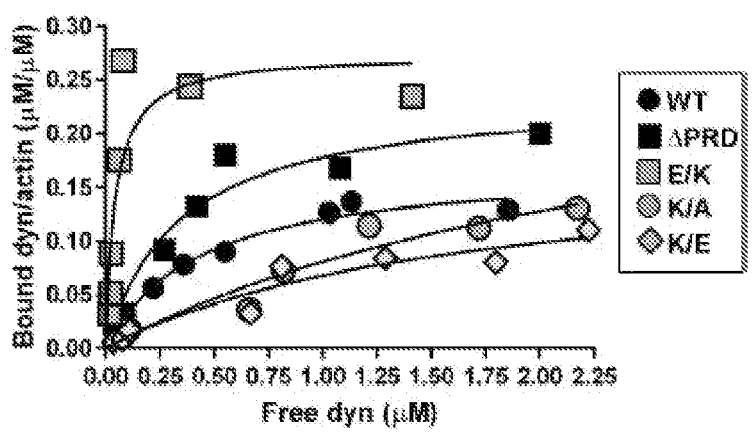

USE OF DYNAMIN RING STABILIZERS

CROSS-REFERENCE TO RELATED APPLICATIONS

The present application is a national stage filing under 35 U.S.C. §371 of PCT/AU2010/000677, filed on 21 May 2010 which in turn claims priority of U.S. Provisional Application No. 61/180,261, filed on 21 May 2009. The disclosures of each of the above applications are hereby incorporated by reference in their entireties into the present application.

SEQUENCE SUBMISSION

The present application includes a Sequence Listing filed in electronic format. The Sequence Listing is entitled 3587103SequenceListingRevised.txt, was created on 25 Jan. 2012 and is 9 kb in size. The information in the electronic format of the Sequence Listing is part of the present application and is incorporated herein by reference in its entirety.

FIELD OF THE INVENTION

The present invention relates to the use of a class of agents referred to herein as "dynamin ring stabilizers" to promote formation of, and/or maintain, stable dynamin rings in cells. The invention has particular application in the prophylaxis or treatment of kidney diseases or conditions characterized by proteinuria.

BACKGROUND OF THE INVENTION

The global epidemic of chronic kidney disease (CKD) is progressing at an alarming rate. Up to 11% of the general population is affected in the US, Australia, Japan and Europe. There is a simultaneous steady increase of type II diabetes, and its associated kidney complications, particularly in India, China and South-East Asia, and kidney-related diseases are eluding present treatment options and resources. Histological and genetic data strongly implicate podocyte dysfunction in glomerular disease (Susztak and Bottinger 2006; Tryggvason et al. 2006).

One of the earliest events marking podocyte dysfunction is disruption of foot processes (FP) and slit diaphragms, which is thought to cause foot-process fusion and proteinuria (Susztak and Bottinger 2006). In most cases of CKD, the first clinical sign is proteinuria. If these early structural changes within podocytes are not reversed, progressive, severe damage occurs, leading to detachment of podocytes from the glomerular basement membrane (GBM). This results in scarring, obliteration of the urinary space, and development of segmental glomerulosclerosis and end stage renal failure. Rearrangement of the actin cytoskeleton which links the slit diaphragm, apical domain and sole plate, serves as a common denominator during foot process (FP) effacement. Thus, a better understanding of mechanisms controlling foot process formation in health and disease is essential to design better early diagnostics and therapies that intervene, while permanent damage may still be preventable.

Renal filtration occurs in the glomerulus, a specialized structure that ensures selectivity of the kidney filter so that water, electrolytes and waste products are passed into the urinary space, while essential plasma proteins are retained in the blood. A sign of glomerular dysfunction is the loss of protein in the urine termed proteinuria or nephrotic syndrome (defined as protein loss exceeding 3.5 grams/day). Proteinuria often leads to progressive renal failure, eventually requiring dialysis or kidney transplantation. Together with the GBM and the glomerular endothelial cells, podocytes form a key component of the kidney permeability barrier. Podocyte function depends on a complex cellular structure, which consists of a cell body, as well as major processes and foot processes (FP) as described above. The FPs of one podocyte are inter-digitated with those of its neighbors, and the intercellular space between adjacent foot processes is bridged by a slit diaphragm composed of the protein nephrin, which also represents the final barrier to protein loss. Thus, podocyte injury is tightly correlated with proteinuria.

Podocyte FPs contain an elaborate and dynamic actin-based cytoskeleton that is essential for their membrane morphogenesis and for establishing and maintaining the filtration barrier in the kidney (Faul et al. 2007). FPs contain a microfilament-based contractile apparatus composed of actin, myosin II, α-actinin, talin, and vinculin, which is linked to the GBM at focal contacts by an integrin α3β1 complex (Faul et al. 2007). The FP actin is organized in two principle forms: a podosome-like, cortical network of short branched actin filaments, and stress fibers composed of an actin:myosin core occupying the center of the FP (Ichimura et al. 2003). FP structure appears to be optimized for constant actin-driven morphological rearrangements, which are essential for glomerular filtration (Moeller and Holzman 2006).

Most forms of proteinuria and nephrotic syndrome involve a reduction of podocyte membrane extensions and transformation of podocyte FPs into a band of cytoplasm (i.e., FP effacement). Changes in FP morphology are primarily driven by reorganization of the actin cytoskeleton, which condenses into a thick bundle against the sole of podocyte foot processes. A number of proteins directly or indirectly alter podocyte cytoskeletal organization. For example, mutations in α-actinin-4, which cause a late-onset form of focal segmental glomerulosclerosis (FSGS), revealed the importance of structural actin binding proteins for podocyte function (Kaplan et al. 2000). Signals that originate at the slit diaphragm can directly influence the actin cytoskeleton in podocytes (Jones et al. 2006; Moeller et al. 2004).

It has been reported that cell focal adhesion turnover is mediated through dynamin-clathrin-dependent endocytosis of activated β1 integrins, and that knockdown of either dynamin II or both clathrin adaptors AP-2 and disabled-2 (DAB2) blocks β1 integrin internalization leading to impaired focal adhesion disassembly and cell migration (Chao and Kunz, 2009).

FP effacement during nephrotic syndrome is a migratory event (Reiser et al. 2004). Cultured podocytes contain all three major categories of actin structures required for cell migration: lamellipodia, filopodia and contractile actin stress fibers. Cultured podocytes also express all known differentiation markers characteristic of podocytes including: nephrin, podocin, CD2AP, synaptopodin, as well as known components of the slit diaphragm such as ZO-1, P-cadherin, α-, β-, and γ-catenin (Mundel et al. 1997; Saleem et al. 2002). Indeed, podocytes have been extensively used to study known actin binding and bundling proteins (e.g., α-actinin 4 and synaptopodin (Asanuma et al. 2005; Asanuma et al. 2006). The cortical actin web that underlies formation of lamellipodia and filopodia in cultured podocytes appears to be equivalent to the short-branched actin web in the vicinity of the plasma membrane observed by EM in podocytes in vivo (Ichimura et al. 2003). Similarly, actin-myosin stress fibers observed in cultured podocytes are likely to be equivalent to non-branched stress fibers occupying the center of FP in vivo (Ichimura et al. 2003).

Cytoskeletal dynamics are often controlled by the Rho family of small GTPases. At the leading edge of cells, Rac1 and Cdc42 promote cell motility through the formation of cortical actin, which in turn promotes motility through the formation of lamellipodia and filopodia, respectively. In contrast, RhoA promotes the formation of contractile actin-myosin-containing stress fibers in the cell body. RhoA signaling plays an important role in regulating the actin cytoskeleton in podocytes. Thus, synaptopodin, an actin-binding protein expressed in podocytes (Mundel et al. 1997) induces stress-fiber formation by extending the lifetime of active RhoA (Asanuma et al. 2006). The exact roles of Rac1 and Cdc42 signaling for podocyte structure and function are less well understood.

It has been reported that in some mouse models of nephrotic syndrome, preservation of dynamin is sufficient to counteract early stages of foot processes effacement and proteinuria (Sever et al. 2007). Dynamin is a large GTPase enzyme that severs membrane-bound clathrin-coated vesicles. The clathrin-mediated endocytic pathway is of special interest to biomedical researchers because it is involved in internalizing activated receptors, sequestering growth factors, antigen presentation, cytokinesis, synaptic transmission and as an entry route for a variety of pathogens. Dynamin comprises three major isoforms: dynamin I (neurons); dynamin II (ubiquitous) and dynamin III (neurons and testes) (Cousin and Robinson 2001). Common to all are five domains, a GTPase domain (required for vesicle fission), a middle domain (MD, of unknown function), pleckstrin homology domain (PH, targeting domain and potentially a GTPase inhibitory module), a GTPase effector domain (GED, which controls dynamin self-assembly into rings), and a proline-rich domain (PRD, which interacts with proteins containing an SH3 domain and is the main site for dynamin I and III phosphorylation in vivo).

Dynamin is best known for its roles in clathrin-mediated endocytosis at the plasma membrane and synaptic vesicle endocytosis in neurons (Sever et al. 2000b). A number of studies indicate that dynamin has additional roles, including regulation of the actin cytoskeleton through molecular mechanisms that are poorly understood (Schafer 2004). Dynamin's role in regulation of the actin cytoskeleton has been attributed to its interactions with known actin binding and regulatory proteins such as profilin, Nck and cortactin (Orth and McNiven 2003; Schafer 2004). A previous study has also indicated that dynamin is essential for formation of functional FPs in podocytes (Sever et al. 2007).

Dynamin exhibits unique biochemical characteristics distinct from other GTPases, such as high molecular weight (MW=100 kDa) and atypically low affinity for GTP ($K_m$=~10 µM). Dynamin exists in three main states—basal, ring or helix—and its GTPase activity increases stepwise upon transition to each state. More particularly:

a) In its "basal" state dynamin is in equilibrium between monomer, dimers and homotetramers (Muhlberg et al. 1997), and has a "basal" GTPase rate of ~1 $min^{-1}$.

b) Dynamin dimers or tetramers can further self-assemble into higher-order structures resembling "rings" that have an outer diameter of about 50 nm and an inner opening of about 30 nm (Hinshaw and Schmid, 1995). This typically occurs above 500 nM dynamin in vitro. The rings are not always closed and the diameter can vary between systems. Ring formation is promoted by dialysis of dynamin into low salt buffers and occurs with high concentrations of dynamin of around 0.5-1 micromolar. Ring formation stimulates dynamin's GTPase activity about 10 fold (Warnock et al. 1996). The increase in the rate of GTP hydrolysis is due to activation of intramolecular GTPase activating domain within dynamin that only becomes active when dynamin tetramers come together (Sever et al. 1999). A dynamin mutant has been reported that is predicted to live longer in the ring form—dynR725A is a mutant impaired in stimulated rate of GTP hydrolysis (Sever et al. 2000a).

c) In the presence of an assembly template dynamin can further assemble into a "helix" in vitro. The helix assembly templates include phospholipid liposomes, lipid nanotubes or microtubules. The helix appears to be an extension of the individual ring structure into a highly elongated helical structure, much like a spring. Helix formation stimulates dynamin's GTPase activity 100-1000 fold (Warnock et al. 1996). The stimulated rate of GTP hydrolysis in turn drives dynamin disassembly in vitro, and leads to loss of positive cooperativity for GTP-binding (Sever et al. 2006).

There is an emerging new field of dynamin pharmacology with the development of small-molecule inhibitors specific for the dynamin family of GTPases as powerful new tools with which to study cellular endocytosis in these systems. Small molecule dynamin inhibitors have attracted widespread attention and have been used to study endocytosis and other aspects of membrane dynamics in a variety of cellular systems (Macia et al. 2006). These inhibitors offer many distinct advantages over traditional means of dynamin inhibition in cells by expression of dynamin GTPase mutants or by small interfering RNA (siRNA)-mediated dynamin knockdown which cannot be used to study rapid cellular effects. Small molecule, cell-permeable inhibitors are able to rapidly block endocytosis in minutes and are readily reversible (Macia et al. 2006; Quan et al. 2007).

The first reported dynamin inhibitors were long chain ammonium salts such as myristyl trimethyl ammonium bromide (MiTMAB), octadecyltrimethyl ammonium bromide (OcTMAB) (Hill et al. 2004) and dimeric tyrphostins such as Bis-T (Hill et al. 2005). Later a series of room temperature ionic liquids (RTILs) (Zhang et al. 2008) and dynasore (Macia et al. 2006) were reported. Finally, indole-based inhibitors termed "dynoles" (Hill et al. 2009) and iminochromene-based inhibitors termed "iminodyns" have been reported (Hill et al. 2010). Most studies screening for dynamin inhibitors use GTPase assays whereby dynamin is maximally stimulated, and likely to be in its helical state. Some of the most potent inhibitors from each of these series are also potent and reversible inhibitors of endocytosis in cells (Quan et al. 2007; Hill et al. 2009; Hill et al 2010).

SUMMARY OF THE INVENTION

Broadly, the invention stems from two discoveries. Firstly, it has been found that a subgroup of dynamin modulators can promote the accumulation of dynamin in its oligomerised ring state and retard dynamin ring disassembly. The compounds in this subgroup are termed "dynamin ring stabilizers". One consequence of prolonging dynamin ring lifetime is that this stimulates basal dynamin GTPase activity, another is that this facilitates the formation of filamentous actin (F-actin). Secondly, it has been found that dynamin directly binds actin via the dynamin middle domain (MD), promoting its oligomerization into rings which have a direct role in de novo formation of focal adhesions and actin filaments in podocytes. Stimulation of dynamin rings (as distinct from dynamin helices) is a new cellular function for dynamin that is separate from its known endocytic role. Prolonging dynamin ring formation and/or lifetime has particular application in the prophylaxis or treatment of foot process effacement in podocytes and proteinuric kidney diseases.

In an aspect of the invention there is provided a method for promoting dynamin ring formation and/or maintenance of dynamin rings in a cell, comprising treating the cell with an effective amount of a dynamin ring stabilizer, or a prodrug or pharmaceutically acceptable salt of the dynamin ring stabilizer.

In another aspect of the invention there is provided a method for prophylaxis or treatment of a kidney disease or condition characterized by proteinuria, comprising administering to an individual in need thereof an effective amount of at least one dynamin ring stabilizer, or a prodrug or pharmaceutically acceptable salt of the dynamin ring stabilizer.

In another aspect of the invention there is provided a method for prophylaxis or treatment of podocyte dysfunction, comprising treating the podocyte with an effective amount of at least one dynamin ring stabilizer, or a prodrug or pharmaceutically acceptable salt of the dynamin ring stabilizer.

Typically, the podocyte dysfunction is characterized by, or is associated with, foot process effacement.

In another aspect of the invention there is provided a method for maintaining or inducing actin cytoskeleton formation in a cell, comprising treating the cell with an effective amount of at least one dynamin ring stabilizer, or a prodrug or pharmaceutically acceptable salt of the dyamin ring stabilizer.

In another aspect of the invention there is provided a method for inducing focal adhesions and/or actin stress fibres in a cell, comprising treating the cell with an effective amount of at least one dynamin ring stabilizer, or a prodrug or pharmaceutically acceptable salt of the dyamin ring stabilizer.

In another aspect there is provided a method of screening a test agent for use as a dynamin ring stabilizer, comprising:
providing the test agent;
incubating the test agent with dynamin protein under conditions suitable for the formation of dynamin rings; and
evaluating whether the test agent promotes accumulation of dynamin rings and/or inhibits disassembly of dynamin rings, the accumulation of dynamin rings and/or inhibition of disassembly of dynamin rings increasing basal dynamin GTPase activity.

The evaluation of whether the test agent promotes the accumulation of dynamin rings or inhibits disassembly of dynamin rings can involve assaying for an increase in basal dynamin GTPase activity, and/or release of dynamin that is indicative of dynamin ring disassembly.

In another aspect of the invention there is provided a dynamin ring stabilizer for use in promoting dynamin ring formation and/or maintenance of dynamin rings in a cell, or a prodrug or pharmaceutically acceptable salt of the dynamin ring stabilizer.

In another aspect of the invention there is provided at least one dynamin ring stabilizer for use in the prophylaxis or treatment of a kidney disease or condition characterized by proteinuria, or a prodrug or pharmaceutically acceptable salt of the dynamin ring stabilizer.

In another aspect of the invention there is provided the use of at least one dynamin ring stabilizer in the manufacture of a medicament for promoting dynamin ring formation and/or maintenance of dynamin rings in cells of an individual in need thereof, or a prodrug or pharmaceutically acceptable salt of the dynamin ring stabilizer.

In still another aspect of the invention there is provided the use of at least one dynamin ring stabilizer in the manufacture of a medicament for prophylaxis or treatment of a kidney disease or condition characterized by proteinuria, or a prodrug or pharmaceutically acceptable salt of the dynamin ring stabilizer.

The dynamin ring stabilizer used in an embodiment of the invention can be any such compound that promotes assembly, or inhibits disassembly, of dynamin rings. The inhibition can be retardation or prevention of dynamin ring disassembly.

By the term "dynamin ring" as used herein is meant a ring of oligomerised dynamin units. The ring can be a closed ring or a single turn of a dynamin helix (helical dynamin).

By the term "dynamin ring stabilizer" as used herein is meant an agent that interacts with dynamin and stimulates basal dynamin GTPase activity in the absence of an assembly template (e.g., microtubules, phospholipid vesicles and/or nanotubes) around which dynamin helices form. A dynamin ring stabilizer promotes dynamin ring assembly and/or inhibits dynamin ring disassembly, both of which may result in dynamin ring accumulation and/or an increase in basal dynamin GTPase activity. Hence, an agent that promotes dynamin ring assembly and/or inhibits dynamin ring disassembly is encompassed by the term "dynamin ring stabilizer" in the context of the present invention. Typically, the dynamin ring stabilizer will be an agent that inhibits dynamin ring disassembly.

The stimulation of basal dynamin GTPase activity by the dynamin ring stabilizer is to a level less than that associated with maximally active helical dynamin whereby maximal activity is achieved in the presence of an assembly template.

The interaction of the dynamin ring stabilizer with dynamin can be binding of the dynamin ring stabilizer to dynamin, or by direct or indirect association of the dynamin ring stabilizer with dynamin. When dynamin is in its helical state, the dynamin ring stabilizer may increase the GTPase activity of individual dynamin rings within that helix, but to a level lower than that achieved by co-operative interaction between dynamin rings.

Most typically, the dynamin ring stabilizer utilized in a method embodied by the invention is an inhibitor of the GTPase activity of maximally stimulated helical dynamin. Likewise, the test agent screened for use as a dynamin ring stabilizer can be an inhibitor of the GTPase activity of helical dynamin. However, from the above it will be understood that the dynamin ring stabilizer need not be an inhibitor of dynamin ring disassembly and indeed, need not be an inhibitor of helical dynamin GTPase activity.

The dynamin with which the dynamin ring stabilizer interacts and/or the dynamin from which the dynamin ring or rings are formed, can be selected from the group consisting of dynamin I (dynI), dynamin II (dynII), dynamin III (dynIII), and dynamin isoforms, and mixtures of the foregoing.

The features and advantages of invention will become further apparent from the following detailed description of non-limiting embodiments together with the accompanying drawings.

BRIEF DESCRIPTION OF THE ACCOMPANYING DRAWINGS

Figure 5:
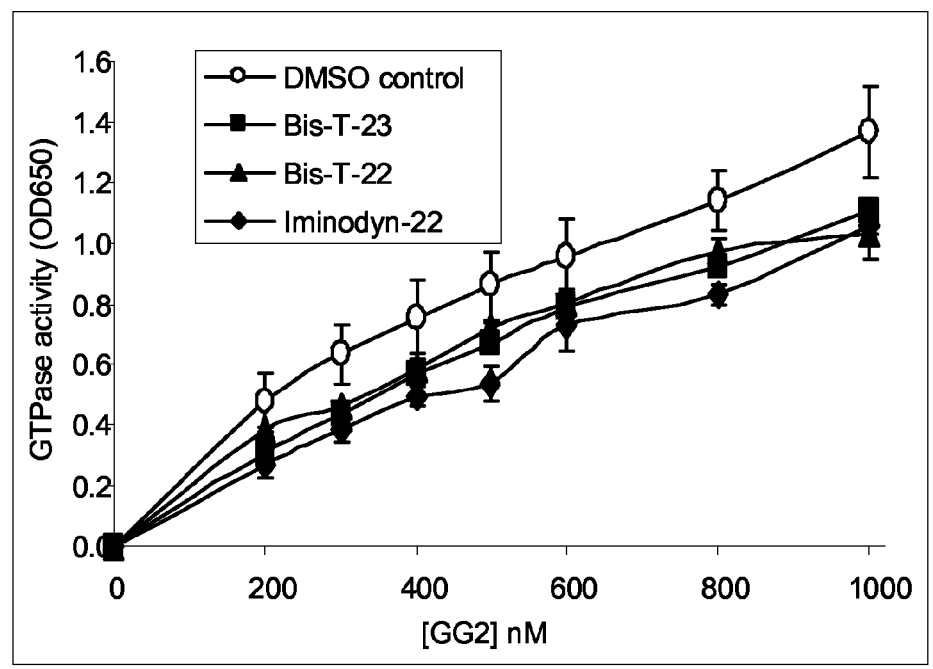

FIG. 5 is a graph showing the basal GTPase activity of the truncated dynamin I construct known as GG2, containing only the GTPase domain linked to a small part of the GED domain (Chappie et al 2009). Unlike full length dynamin this construct is known to be unable to self-assemble or to form rings. Bis-T-22 and -23 and imminodyn-22 have no effect on the basal activity of this assembly-incompetent construct.

Figure 6:
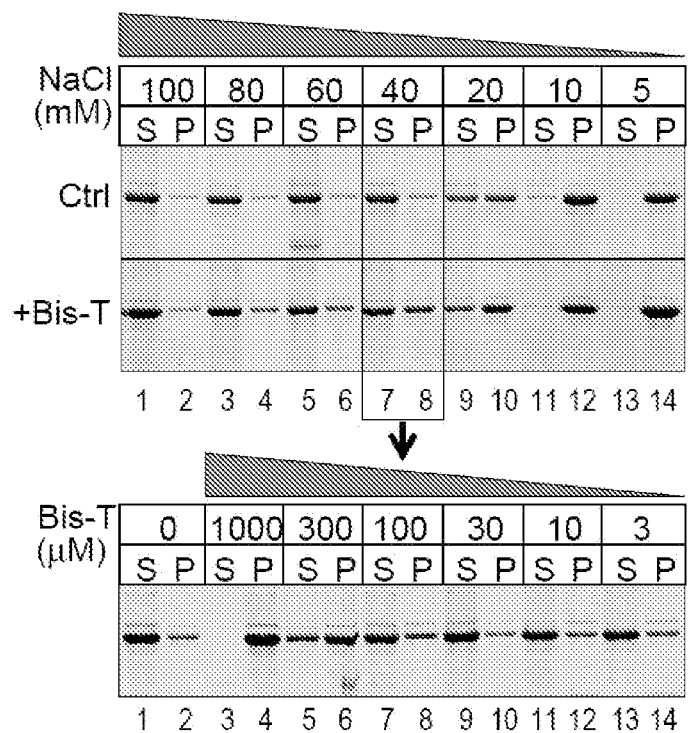

FIG. 6 shows that Bis-T-22 at high concentration [dyn] (520 nM) promotes dynamin ring self-assembly.

Figure 7:
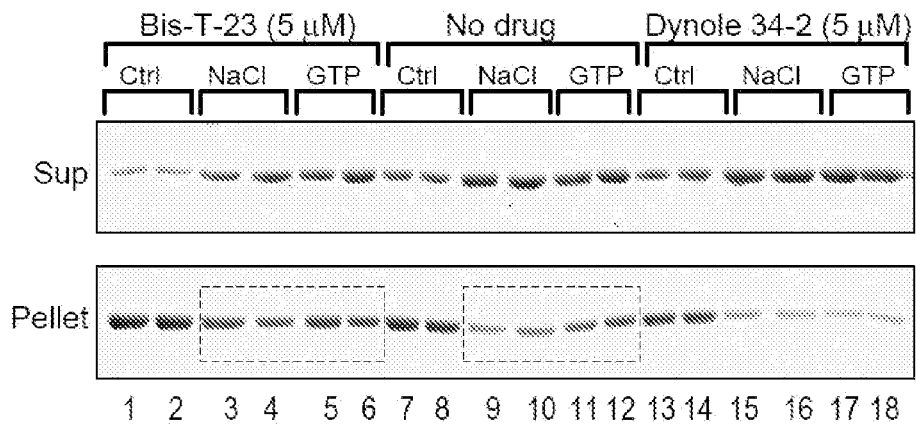

FIG. 7 shows that Bis-T-23 prevents dynamin disassembly.

Figure 8:
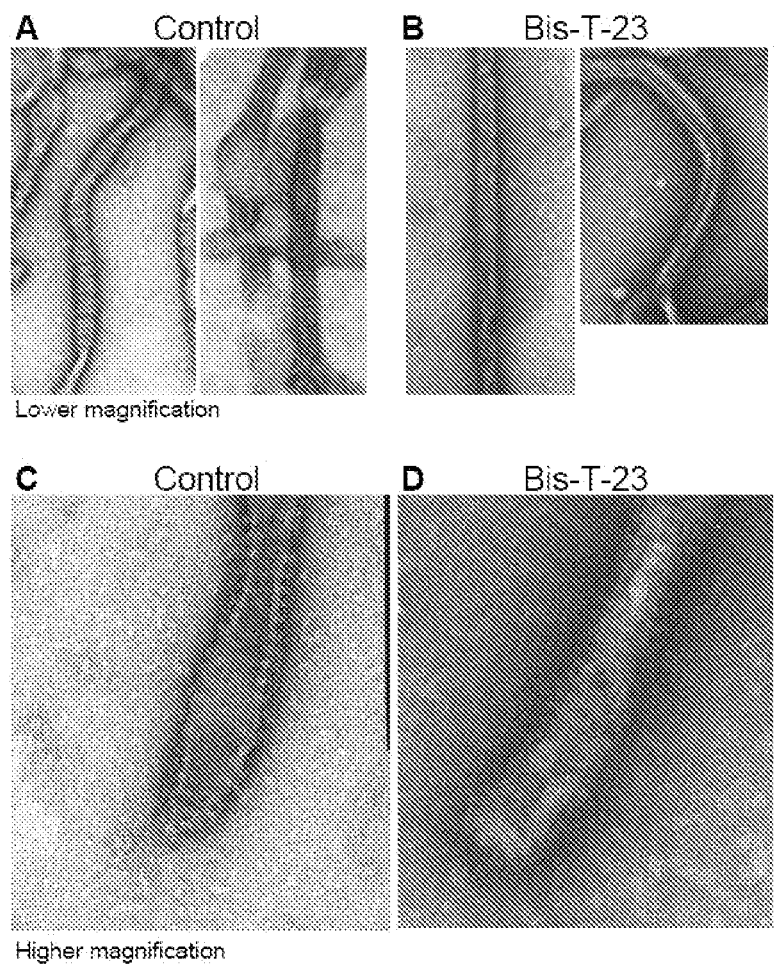

FIGS. 8 (A) to (D) are electron micrographs showing Bis-T-23 prevents constriction or helical expansion of dynamin on PS liposomes in vitro. It stabilizes the dynamin helix, which loses its flexibility and forms uniform diameter rings, inhibiting dynamin ring disassembly.

FIG. 9 shows the effect of treating purified full length dynamin I with Bis-T-23 in the absence of a template. Dynamin was then examined by electron microscopy. Dynamin rings are specifically induced by Bis-T-23 (5.4 µM, A). The rings are bona fide dynamin rings (B). Quantitative analysis shows a 6-fold increase in bona fide rings (C).

FIG. 10 shows that Bis-T-22 (100 µM for 30 minutes) induces clathrin coated pits in cells that have unusually long necks and are encircled by rings in both cultured human lymphoblast cells (A) or rat brain synaptosomes (B).

FIG. 11 (A) is a graph showing Bis-T-23 and two "dyngo" series dynamin inhibitors are dynamin ring stabilizers. Dyngo-7a is also known as dynasore. Dynamin I (50 nM) GTPase stimulation was performed in the absence of the detergent Tween-80 (and in the absence of any known activators such as PS liposomes, nanotubes or microtubules). In contrast, dynole 34-2, a potent dynamin inhibitor, does not stimulate basal dynamin activity under these conditions. B) is a graph showing variety of potent dynamin inhibitors are activators of basal dynamin GTPase activity (Bis-T series compounds were used at a conc. of 10 µM, all other compounds were used at a conc. of 30 µM). All of the compounds tested inhibited phosphatidylserine (PS)-stimulated dynamin between 300 nM-3 µM (data not shown). The GTPase activity of dynamin I (dynI; 200 nM) was measured in the absence of lipid activators (and in the presence of standard Tween-80 at 0.06%).

FIG. 12 shows detection of direct dynamin-actin interactions using standard co-sedimentation assays in which F-actin sediments under high-speed centrifugation.

FIG. 13 shows amino acid sequence alignments between dynamin II (dyn2) (splice variants a and b) (SEQ ID No. 1 and SEQ ID No. 2), dynamin I (dyn1) (splice variants a and b) (SEQ ID No. 3 and SEQ ID No. 4), *Drosophila* (Shi) (SEQ ID No. 5), *C. elegans* (Cele) (SEQ ID No. 6), yeast (Vps1) (SEQ ID No. 7). Dnm1 (SEQ ID No. 8), 'loss of function' mutants DynK/E (SEQ ID No. 9) and Dyn K/A (SEQ ID No. 10), and 'gain of function' mutant Dyn E/K (SEQ ID No. 11). Dnm1 is a dynamin family member involved in mitochondrial morphogenesis.

FIG. 14 shows a Scatchard Plot of the direct dynamin and F-actin interactions. Increasing concentrations of dynamin (free) were added to 5 µM of F-actin. After centrifugation at 100,000×g proteins were separated on SDS-PAGE and bands were analyzed using densitometry.

Figure 15:
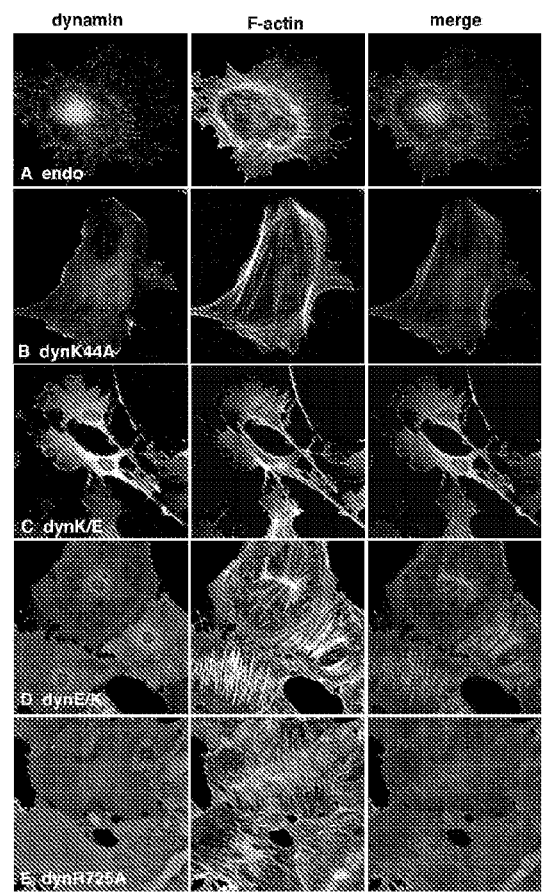

FIGS. 15 (A-E) are photographs illustrating that dynamin-actin interactions are essential for organization of the actin cytoskeleton in podocytes. Podocytes were infected with viruses expressing dynamin mutants as indicated. The actin cytoskeleton appears greatly increased in the cells expressing dynE/K and dynR725A.

Figure 16:
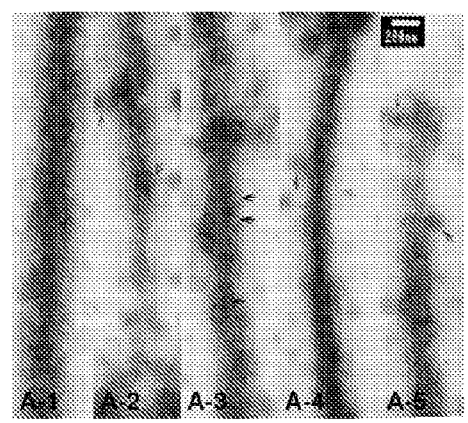

FIG. 16 shows assembled dynamin rings cross-link actin filaments into thin bundles in the presence of GTPγS. Actin filaments were visualized using negative staining and electron microscopy. Arrows point toward dynamin rings along the bundled filaments.

Figure 17:
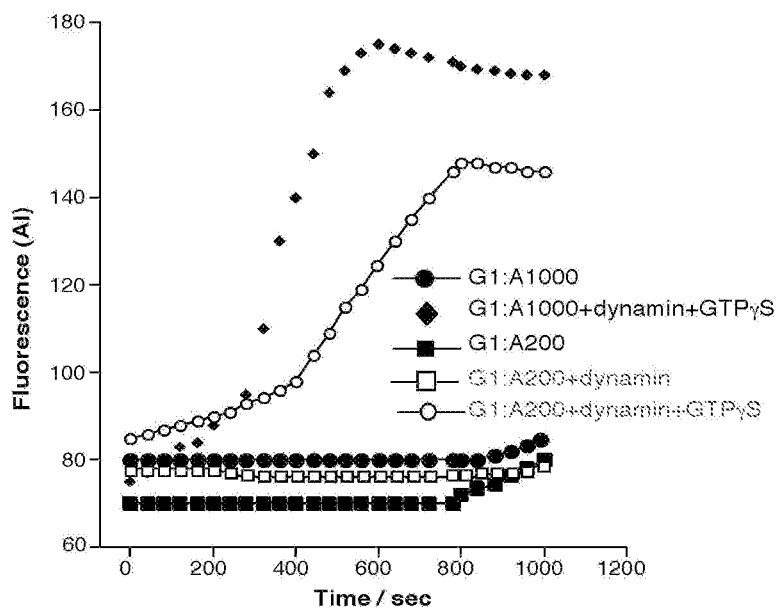

FIG. 17 is a graph showing dynamin rings promote actin polymerization. Representative time courses of the repolymerization of actin when 0.33 µM Gsn-actin complexes (G1:200A or G1:1000A) are incubated in the absence and presence of 0.1 µM dynamin with or without 100 µM GTPγS.

Figure 18:
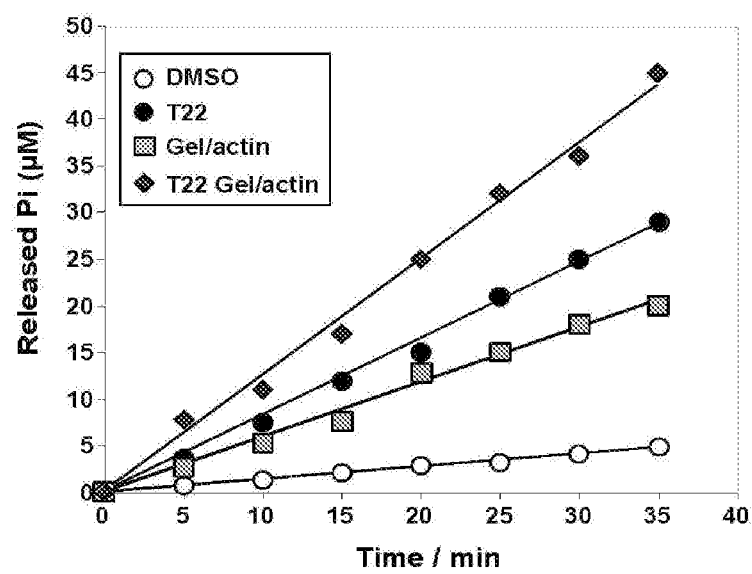

FIG. 18 is a graph showing the dimeric benzylidenemalonitrile tyrphostin Bis-T-22 stimulates dynamin's basal rate of GTP hydrolysis. Shot gelsolin-capped F-actin also stimulates dynamin's basal rate of GTP hydrolysis. Time course for basal GTP hydrolysis of 0.2 µM dyn1 incubated without or with 7 µM Bis-T-22, and with or without 10 µM Gsn-F-actin complexes. The effects of Bis-T-22 and Gsn-F-actin are at least additive.

Figure 19:
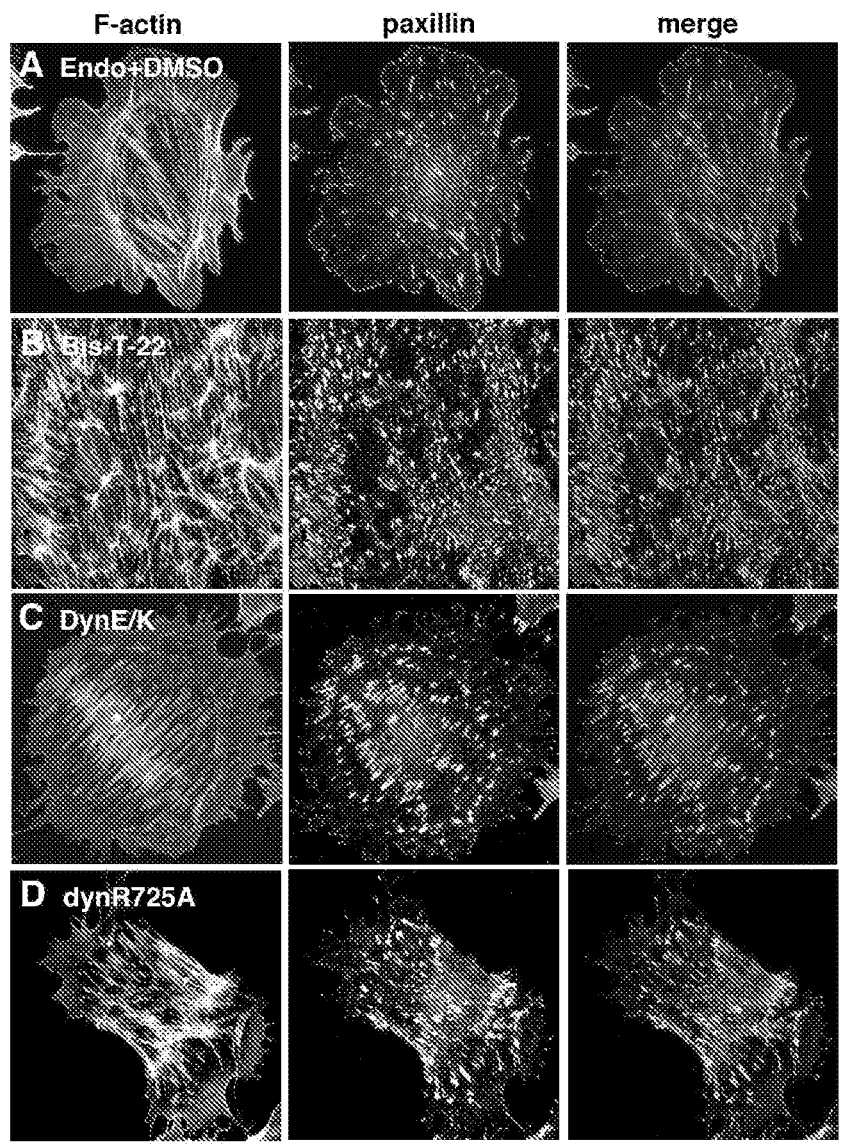

FIG. 19 is a photograph showing the effects of Bis-T-23 on the actin cytoskeleton in podocytes. Cells were stained using rhodamine-phalloidin for F-actin (left column) and anti-paxillin monoclonal antibody (centre column). The merged staining is shown on the right column. The actin cytoskeleton and focal adhesions are greatly increased in number and amount in the cells treated with Bis-T-23 and cells expressing dynamin mutants, dynE/K and dynR725A.

Figure 20:
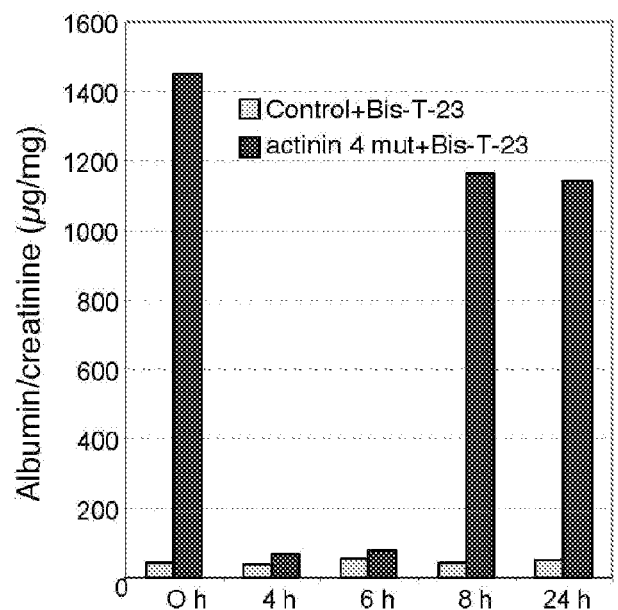

FIG. 20 is a graph showing a control mouse and a mouse expressing 'gain of function' α-actinin 4 mutant protein were injected intraperitoneally with Bis-T-23 (100 µg/100 g body weight). Proteinuria was measured using mouse Albumin-specific ELISA and Creatinine Companion assay kits (Exocell and Bethyl Laboratories) following manufacturer's protocols. A decrease in proteinuria to wild-type levels was obtained up to 6 hours after drug administration.

Figure 21:
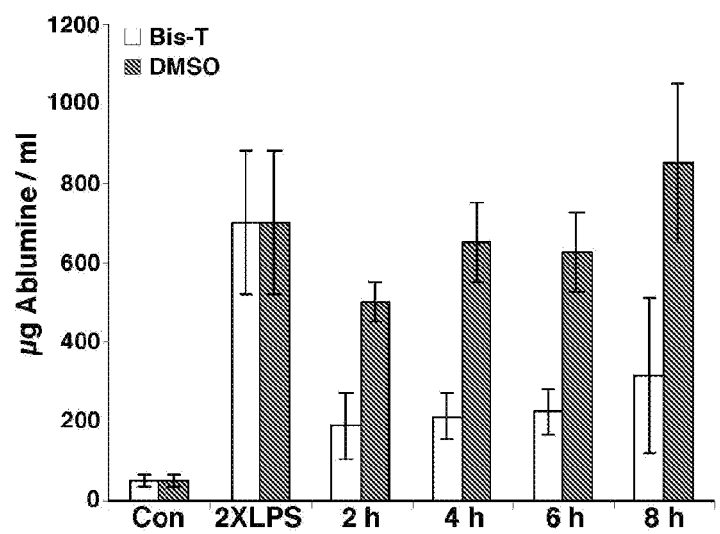

FIG. 21 is a graph showing that the ring stabilizer Bis-T-23 rescues proteinuria in lipopolysaccharide (LPS) treated mice. LPS is a model for proteinuric kidney disease. Albumin levels were determined in 6 mice prior to (Con), 24 hours after LPS injection (2×LPS), and 2, 4, 6 and 8 h after administration of Bis-T-23 (open bars) or DMSO (delivery solution, grey bars). A decrease in proteinuria was noted from 2-8 hours after administration of a single dose of this ring stabilizer.

DETAILED DESCRIPTION OF EXEMPLARY EMBODIMENTS OF THE INVENTION

A subgroup of dual-specificity dynamin modulators has been found to exist among the broader group of dynamin inhibitors. The compounds in this subgroup are "dynamin ring stabilizers" as they inhibit dynamin ring disassembly thereby prolonging dynamin ring lifetime and promoting dynamin ring accumulation. This is consistent with the fact that GTP hydrolysis is known to drive dynamin disassembly (Sever et al. 2006). However, while these compounds reduce the massive GTPase activity of helical dynamin, they can simultaneously increase the basal GTPase activity of individual dynamin rings.

A dynamin ring is a single turn of oligomerized dynamin or in the case of helical dynamin (a dynamin helix), a single turn of the helix. Dynamin rings were first observed in vitro (Hinshaw and Schmid. 1995). They typically have an outer diameter of approximately 50 nm and an inner diameter of about 30 nm, and the rings can be open or closed. Helical dynamin is also known as a dynamin helix, nano-spring, spiral or "stack of rings" (Stowell et al. 1999). Cryo-electron microscopy indicates that dynamin ring size is flexible and can comprise 13-15 asymmetric repeated dynamin units, suggesting that a single ring of helical dynamin comprises 26-30 dynamin molecules (dynamin units) (Zhang and Hinshaw. 2001). However, since the ring diameter is flexible, these numbers are not fixed.

A dynamin ring stabilizer useful in a method embodied by the invention may for instance be selected from the group consisting of helical dynamin GTPase inhibitors, monomeric tyrphostins, dimeric tyrphostins and particularly dimeric benzylidenemalonitrile tyrphostins, iminochromenes, 3-substituted naphthalene-2-carboxylic acid (benzylidene) hydrazides, polypeptides and peptides as further described below.

Suitable dimeric benzylidenemalonitrile tyrphostins (Bis-T) and related compounds that may find application as dynamin ring stabilizers in accordance with embodiments of the invention are described in International Patent Application No. PCT/AU2004/001624 (WO 2005/049009) and Hill et al. 2005, the contents of which are incorporated herein in their entirety.

Bis-tyrphostin-22 (Bis-T-22) is one such dimeric typhostin and is a potent in vitro inhibitor of dynamin when dynamin is activated by phosphatidylserine (PS) liposomes to assemble into a flexible helix. In the absence of PS liposomes, dynamin can only assemble into single rings. Surprisingly, while Bis-T-22 inhibits the activity of helical dynamin it also uniquely, simultaneously stimulates basal dynamin GTPase activity by preventing disassembly of dynamin rings. The structure of Bis-T-22 is shown below. Bis-T has the same structure as Bis-T-22 but has an additional hydroxyl substituent on the C5 carbon atom of each terminal phenyl group.

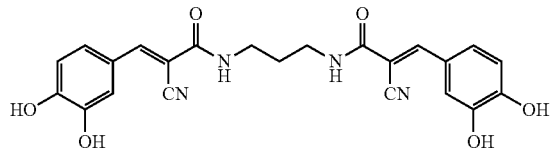

Structure of bis-tyrphostin (Bis-T-22)

Particularly suitable dimeric tyrphostins useful as dynamin ring stabilizers include those Bis-T compounds in which two of the C3-C5 carbon atoms of at least one terminal phenyl ring have hydroxyl (OH) substituents, preferably in a catechol arrangement (e.g., as in Bis-T-22), or all three of the carbon atoms are substituted with hydroxyl (e.g., as in Bis-T-23). Examples include 2-cyano-N-{3-[2-cyano-3-(3,4-dihydroxyphenyl)-acryloylamino]-ethyl}-3-(3,4-dihydroxyphenyl)-acrylamide, 2-cyano-N-{3-[2-cyano-3-(3,4,5-trihydroxyphenyl)-acryloylamino]-ethyl}-3-(3,4,5-trihydroxyphenyl)-acrylamide, 2-cyano-N-{3-[2-cyano-3-(3,4-dihydroxy-4-methoxyphenyl)-acryloylamino]-ethyl}-3-(3,4-dihydroxy-5-methoxyphenyl)-acrylamide, 2-cyano-N-{3-[2-cyano-3-(3,4-dihydroxyphenyl)-acryloylamino]-propyl}-3-(3,4-dihydroxyphenyl)-acrylamide (Bis-T-22), 2-cyano-N-{3-[2-cyano-3-(3,4,5-trihydroxyphenyl)-acryloylamino]-propyl}-3-(3,4,5-trihydroxyphenyl)-acrylamide (Bis-T-23), 2-cyano-N-{3-[2-cyano-3-(3,4-dihydroxy-5-methoxyphenyl)-acryloylamino]-propyl}-3-(3,4-dihydroxy-5-methoxyphenyl)-acrylamide, 2-cyano-N-{3-[2-cyano-3-(3,4-dihydroxyphenyl)-acryloylamino]-butyl}-3-(3,4-dihydroxyphenyl)-acrylamide, 2-cyano-N-{3-[2-cyano-3-(3,4,5-trihydroxyphenyl)-acryloylamino]-butyl}-3-(3,4,5-trihydroxyphenyl)-acrylamide, 2-cyano-N-{3-[2-cyano-3-(3,4-dihydroxy-5-methoxyphenyl)-acryloylamino]-butyl}-3-(3,4-dihydroxy-5-methoxyphenyl)-acrylamide, 2-cyano-N-{3-[2-cyano-3-(3,4-dihydroxyphenyl)-acryloylamino]-pentyl}-3-(3,4-dihydroxyphenyl)-acrylamide, 2-cyano-N-{3-[2-cyano-3-(3,4,5-trihydroxyphenyl)-acryloylamino]-pentyl}-3-(3,4,5-trihydroxyphenyl)-acrylamide, 2-cyano-N-{3-[2-cyano-3-(3,4-dihydroxy-5-methoxyphenyl)-acryloylamino]-pentyl}-3-(3,4-dihydroxy-5-methoxyphenyl)-acrylamide, 2-cyano-N-{3-[2-cyano-3-(3,4-dihydroxyphenyl)-acryloylamino]-hexyl}-3-(3,4-dihydroxyphenyl)-acrylamide, 2-cyano-N-{3-[2-cyano-3-(3,4,5-trihydroxyphenyl)-acryloylamino]-hexyl}-3-(3,4,5-trihydroxyphenyl)-acrylamide, and 2-cyano-N-{3-[2-cyano-3-(3,4-dihydroxy-5-methoxyphenyl)-acryloylamino]-hexyl}-3-(3,4-dihydroxy-5-methoxyphenyl)-acrylamide.

Further dynamin ring stabilizers include those in which a substituent on the C2 carbon atom of at least one terminal phenyl ring of a Bis-T compound and the position occupied by an adjacent cyanyl group (CN) are cyclised as described in WO 2005/049009. For instance, when the substituent is hydroxy, the hydroxy group can react with the cyanyl group to form an iminochromene as follows:

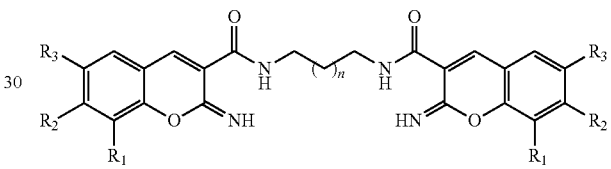

where for example, $R_1$ is OH, $R_2$ is OH and $R_3$ is H; $R_1$ is H, $R_2$ is OH and $R_3$ is OH; or $R_1$, $R_2$ and $R_3$ are OH; and n is usually 0, 1, 2 or 3, and most usually 1. Further examples of iminochromenes useful in embodiments of the invention are described below (see Table 2). Analogs of Bis-T or iminochromene compounds as described above in which at least one of the ring oxygen atoms and/or at least one of the NH groups and/or backbone oxygen atoms of the compound are subjected to bioisostere replacement may also be used (e.g., see Lima and Barreiro. 2005, the contents of which is incorporated herein in its entirety by cross-reference).

In addition, asymmetric analogues of the above dimeric compounds may be utilized. Examples include the asymmetric azido and diazarinyl analogs of dimeric tyrphostins described by Odell et al. 2009. Moreover, monomeric tyrphostin analogs of the dimeric tyrphostins exemplified above can be utilized. However, in the case of these tyrphostins, they are not GTPase inhibitors (e.g., see Hill et al. 2005).

Yet further examples of dynamin ring stabilizers include 3-hydroxynaphthalene-2-carboxylic acid (3,4-dihydroxybenzylidene) hydrazide (dynasore) and analogs thereof. The structure for dynasore is as follows.

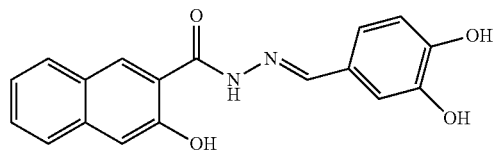

Structure of Dynasore

Dynasore was discovered in a library screen using recombinant dynamin I activated by the SH3 domain containing protein grb2 (Macia et al. 2006). The structure of dynasore is superficially similar to that of Bis-T-22 where the position and number of the hydroxyls around the terminal phenyl ring of Bis-T-22 was found to contribute significantly to the dynamin inhibitory potency of the compound. Examples of further 3-substituted naphthalene-2-carboxylic acid (benzylidene) hydrazide analogs of dynasore (named dyngo compounds herein) found to exhibit improved dynamin inhibitory potency compared to dynasore are shown in Table 1. Each of the dyngo compounds was synthesized by a simple one-step condensation reaction coupling 3-hydroxy-2-naphthoic acid hydrazide with a variety of hydroxyl substituted benzaldehydes affording a focussed library as illustrated by Scheme 1 below (e.g., by mixing the reagents in ethanol (e.g., 10 ml) in a round bottomed flask, refluxing the mixture for 2 hours, allowing it to cool and removing the solvent in vacuo prior to recrystallizing the product from ethanol although other synthesis methods available). In particular, Table 1 shows the structure of each dyngo compound, its molecular weight (MW) and $IC_{50}$ for inhibition of native brain dynamin I GTPase activity stimulated by PS liposomes in the presence or absence of Tween 80.

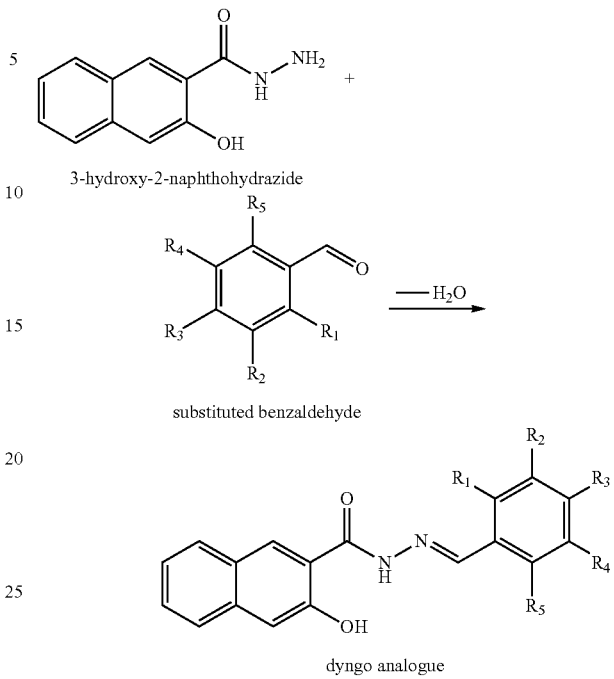

Scheme 1: Synthesis of dyngo compounds

TABLE 1

| | Dyngo compounds | | | |
|---|---|---|---|---|
| Compound | Structure | MW (g/mol) | $IC_{50}$ (μM) | $IC_{50}$ (μM) |
| Dynasore (Dyngo-7a) | | | Full-length Dyn I (7 nM, 2 μg/mol PS) With tween 80 | Full-length Dyn I (7 nM, 2 μg/ml PS) Without tween 80 |
| Dyngo-4a | | 338.32 | 2.7 ± 0.7 | 0.31 ± 0.05 |
| Dyngo-6a | | 322.31 | 19.8 | 22.1 |
| Dyngo-1a | | 322.31 | 200 | 7.3 |

TABLE 1-continued

Dyngo compounds

| Compound | Structure | MW (g/mol) | IC$_{50}$ (μM) | IC$_{50}$ (μM) |
|---|---|---|---|---|
| Dyngo-5a | 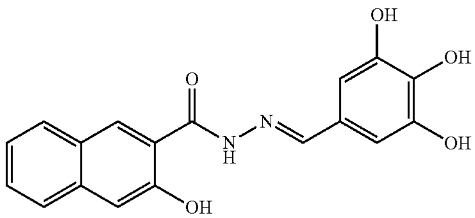 [SMILES: O=C(N/N=C/c1cc(O)c(O)c(O)c1)c1cc2ccccc2cc1O] | 338.32 | ~468 | 4.4 |
| Dyngo-2a | 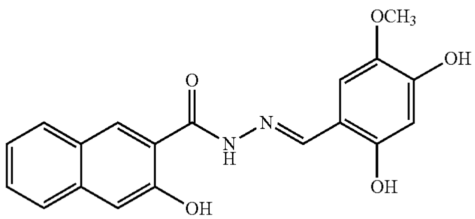 [SMILES: COc1cc(/C=N/NC(=O)c2cc3ccccc3cc2O)c(O)cc1O] | 352.35 | 1170 | 3.6 |
| Dyngo-3a | 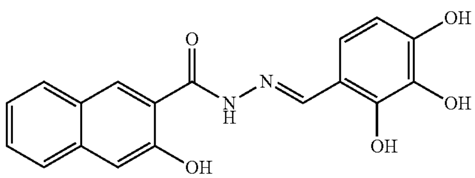 [SMILES: O=C(N/N=C/c1ccc(O)c(O)c1O)c1cc2ccccc2cc1O] | 338.32 | Not Active | 3.1 |
| Dyngo-8a | 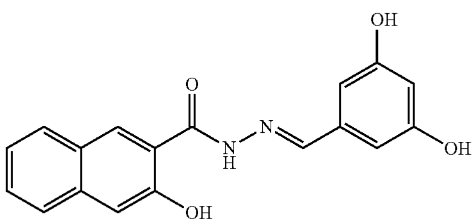 [SMILES: O=C(N/N=C/c1cc(O)cc(O)c1)c1cc2ccccc2cc1O] | 322.31 | Not Active | 39.8 |

A dynamin ring stabilizer which stimulates the basal activity of dynamin or inhibits disassembly of dynamin rings as described herein will typically have a terminal phenyl group with hydroxyl substituents on at least two of three consecutive carbon atoms of the phenyl ring, as in Bis-T-22 and Bis-T-23. However, while the terminal phenyl groups of the above exemplified dimeric tyrphostin, iminochromene and dyngo analogs are substituted with hydroxyl groups, persons of ordinary skill in the art will appreciate one or more of those hydroxyls may be subjected to bioisosteric replacement (such as but not limited to, an —NH$_2$ group or a halo atom such as F, Cl, Br or I, and the like). Likewise, a person of ordinary skill in the art will also recognize that other changes may be made to the dimeric benzylidenemalonitrile tryphostin, iminochromene, monomeric tyrphostin, dynasore and dyngo compounds described above such that dynamin ring stabilizing activity of the compound is retained or enhanced, and any such analogs and modified forms thereof can be used in a method as described herein. Examples of modifications include, but are not limited to replacement of one or more backbone ring carbon atoms for heteroatom(s) (e.g., independently selected from O, N and S) and/or other modifications to those ring systems. The naphthalene group of the dyngo compounds exemplified above is particularly amenable to such modifications and/or bioisoteric replacement, and a large number of modified such compounds useful in methods embodied by the invention are possible. Such modifications and bioisosteric replacements as described above are well within the scope of a person of ordinary skill in the art (e.g., see Lima and Barreiro. 2005) and all are expressly encompassed by the present invention. Indeed, any suitable physiologically acceptable dynamin ring stabilizer can be employed. Further suitable such compounds for use in herein may be identified by screening chemical compound and combinatorial libraries, such screening being well within the scope of the addressee.

Suitable iminochromenes (termed "iminodyns" herein) and related compounds that may find application as dynamin ring stabilizers in accordance with embodiments of the invention are described in Hill et al. 2010, the contents of which are incorporated herein in its entirety by cross-reference.

Iminodyn-22 is one such iminochromene and is a potent in vitro inhibitor of dynamin when dynamin is activated by phosphatidylserine (PS) liposomes to assemble into a flexible helix. While iminodyn-22 inhibits the activity of helical dynamin it also simultaneously stimulates basal dynamin GTPase activity by preventing disassembly of dynamin rings. The structure of iminodyn-22 is shown below.

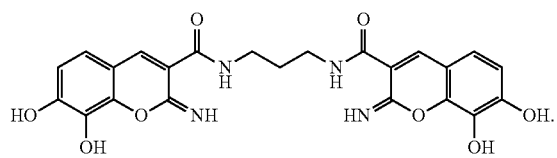

Structure of iminodyn-22

The pathway for synthesis of the iminodyns is shown below in Scheme 2.

Scheme 2: Reagents and conditions for generation of the iminodyns:
i) Ethanol, piperidine (cat.) reflux 2 hr

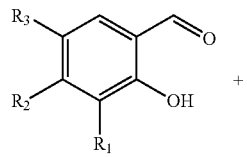

7-12
$R_1, R_2, R_3$ = H or OH

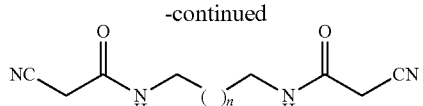

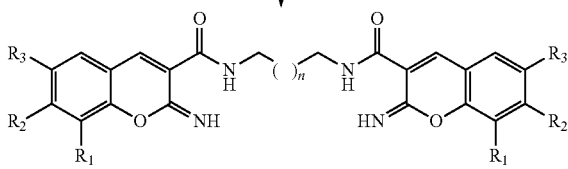

14-38

The structure of iminochromene is distinct from that of Bis-T-22 but the position and number of the hydroxyls around the terminal phenyl rings of contribute significantly to the dynamin inhibitory potency of the compound. Examples of further analogs of iminochromene are shown in Table 2. The table shows the structure of each compound, its $IC_{50}$ for inhibition of native brain dynamin I (at 20 nM) GTPase activity stimulated by PS liposomes. The table also shows the stimulation of basal dynamin I (at 200 nM) GTPase activity in the absence of liposomes.

TABLE 2

Inhibition of dynamin I in vitro GTPase activity, and ring stabilizer activity of iminodyns 17, and 20-23

| Iminodyn compound | Iminodyn structure | PS-stimulated Dyn I GTPase activity $IC_{50}$ (μM) | Ring stabilizer: Dyn I (no PS) $EC_{50}$ (μM) |
|---|---|---|---|
| 17 | | 0.33 ± 0.07 | 31 |
| 20 | | 36.6 ± 7.2 | Not Active |
| 21 | | 17.3 ± 1.0 | 40 |
| 22 | | 0.45 ± 0.05 | 1 |

TABLE 2-continued

Inhibition of dynamin I in vitro GTPase activity, and ring stabilizer activity of iminodyns 17, and 20-23

| Iminodyn compound | Iminodyn structure | PS-stimulated Dyn I GTPase activity IC$_{50}$ (µM) | Ring stabilizer: Dyn I (no PS) EC$_{50}$ (µM) |
|---|---|---|---|
| 23 | (structure: bis-coumarin-carboxamide linked by propylene diamine, with HO groups) | 0.26 ± 0.08 | 4 |

In another form, the dynamin ring stabilizer may be a peptide, polypeptide or an active fragment or modified form thereof which has dynamin ring stabilizing activity. Typically, a dynamin ring stabilizer as described herein is other than a wild-type or modified form of dynamin or a fragment thereof. Examples of polypeptides or peptides that may be used include actin (particularly F-actin), isoforms and/or fragments thereof that provide an actin binding domain for one or more of the dynamin isoforms or for dynamin rings, that promote/stimulate the formation of dynamin rings and thereby act as a dynamin ring stabilizer in the context of the invention. Further, modified forms may be provided in which one or more amino acids are added, substituted or deleted compared to the wild type actin, isoforms and fragments thereof substantially without adversely impacting on its/their capacity to interact with dynamin and promote the accumulation of dynamin rings as described herein, and the use of all such modified forms is also expressly encompassed.

Strategies for identifying such proteinaceous agents suitable for use in methods of the present invention include large scale screening techniques. For instance, phage display library protocols provide an efficient way of screening a large number of potential agents. The library utilised can be a peptide display library expressing randomised peptide sequences fused to a coat protein of the relevant phage utilised, or a library displaying variable domains of antibodies (e.g., Fv fragments). Phages which bind to dynamin can be recovered and amplified by infection of host bacteria. Each clone isolated in this way expresses a specific peptide or antigen-binding particle. The genes encoding the peptide or antigen-binding particle are unique to each phage and can be identified by recovering the DNA of the selected phage clone, sequencing the DNA and comparing the sequence obtained with the known sequence of the phage coat protein expressing the peptide or antigen-binding molecule. The identified DNA can then be used for expression of the encoded proteinaceous agent or modified to provide other such agents utilising recombinant techniques well known in the art.

A compound (whether a dynamin inhibitor or not) can be identified as a dynamin ring stabilizer by assaying for its capacity to promote accumulation of dynamin rings and/or to inhibit disassembly of dynamin rings. This can primarily be determined by incubating the test agent with full length dynamin under conditions in which dynamin rings do not form of their own accord, and assaying for an increase in basal dynamin GTPase activity to a level indicative of the formation or accumulation of dynamin rings relative to control(s). GTPase activity of dynamin or dynamin rings can be determined by any conventionally known method (e.g., see Quan and Robinson. 2005). Such conditions include: (a) the absence of a helix assembly template such as liposomes, microtubules or lipid nanotubes, and (b) higher concentrations of dynamin than normally required for detecting template stimulated activity, typically 50-500 nM dynamin instead of 1-20 nM. Thus, ring stabilizer activity can be identified by the ability to stimulate the GTPase activity of full length dynamin in the absence of other stimulatory factors (such as PS liposomes, microtubules or nanotubes). Additional defining characteristics are available but are not essential if the first condition has been met. One such additional characteristic of ring stabilizer activity is that the stimulated activity occurs after a lag phase of a few minutes, rather than being an immediate activation in vitro. Another characteristic is that a ring stabilizer cannot stimulate the activity of a dynamin construct that is not capable of self-assembly, such as a mutant dynamin or a construct containing the GTPase domain and only a fragment of the GED domain (e.g., GG2 or GG5; Chappie et al 2009). Yet another characteristic of ring stabilizer activity is the ability of the compound to promote the formation of dynamin rings as detected by electron microscopy at such concentrations of dynamin whereby it does not form rings of its own accord. Such conditions typically mean utilising 50-200 nM dynamin in the absence of a template as distinct from higher concentrations where self-assembly is known to occur without the addition of a dynamin ring stabilizer.

An in-cell indicator of ring stabilizer activity is the induction of actin stress fibres and focal adhesions after application of the compound to cultured podocytes or NIH3T3 cells. The induction of podocyte foot processes can also be assessed as an indicator of the accumulation of dynamin rings and/or inhibition of dynamn ring disassembly.

A peptide or polypeptide dynamin ring stabilizer may include D-amino acid(s) and/or be C-terminal and/or N-terminal protected against proteolytic digestion (e.g., "pegylated" with polyethyleneglycol (PEG)). Moreover, peptide or polypeptide dynamin ring stabilizers can be coupled to a "facilitator moiety" for facilitating passage or translocation of the peptide/polypeptide stabilizer across the outer cell/plasma membrane into the cytoplasm of cells, such as a carrier peptide which has the capacity to deliver cargo molecules across cell membranes in an energy-independent manner. Carrier peptides that are known in the art include penetratin and variants or fragments thereof, human immunodeficiency virus Tat derived peptide, transportan derived peptide, signal peptides and fragments thereof which retain the ability to pass across the outer cellular membrane to effect delivery of the attached peptide or other agent into the cell. Rather than a carrier peptide, the facilitator moiety can be a lipid moiety or other non-peptide moiety which enhances cell membrane solubility of the dynamin ring stabilizer, such that passage of the peptide/polypeptide across the cell membrane is effected. The lipid moiety can for instance be selected from triglycerides, including mixed triglycerides. Fatty acids and particularly, saturated $C_{16}$-$C_{20}$ fatty acids may also be used (e.g., stearic acid). A peptide or polypeptide dynamin ring stabilizer can be linked to the facilitator moiety in any conventionally known manner. For instance, the peptide or polypeptide can be linked directly to a carrier peptide through an amino acid linker sequence by a peptide bond or non-peptide covalent bond using a cross-linking reagent. Moreover, chemical ligation methods may be used to create a covalent bond between the carboxy terminal amino acid of the carrier peptide or linker sequence and the peptide or polypeptide dynamin ring stabilizer.

The induction of focal adhesions in cells as described herein may render the cells less able to migrate due to the resulting increase in cell to cell interactions with neighbouring cells. As such, the induction of focal adhesions in podocytes or other cells may also have application in the prophylaxis or treatment of cancer (by inhibiting cancer cell metastasis), and other diseases or conditions responsive to the induction of cell focal adhesions.

Any suitable cell can be treated with a dynamin ring stabilizer, or a prodrug or pharmaceutically acceptable salt thereof, to promote the formation of and/or for maintenance of dynamin rings in the cell as described herein. An embodiment of this aspect of the invention may include selecting the dynamin ring stabilizer (or prodrug or pharmaceutically acceptable salt thereof) to effect the formation of the dynamin rings and/or maintenance of the dynamin rings in the cell. The promotion and/or maintenance of dynamin rings in, for example, podocytes has particular application in the prophylaxis or treatment of kidney diseases or conditions characterized by proteinuria.

The kidney disease or condition characterized by proteinuria for which the dynamin ring stabilizer is administered in accordance with an embodiment of the invention can be selected from, but is not limited to, the group consisting of nephrotic syndrome, chronic kidney disease, glomerular disease, glomerular dysfunction, glomerulonephritis including post-infectious glomerulonephritis and mesangioproliferative glomerulonephritis, nephropathy including diabetic nephropathy and HIV-associated nephropathy, podocyte dysfunction including podocyte damage and podocyte injury, podocytopathies, podocyte foot process effacement, diffuse mesengial sclerosis, congenital nephrotic syndrome (e.g., of the Finnish type (CNSF)), Alpor's syndrome and variants (Alport+), minimal change disease, focal segmental glomerulosclerosis (FSGS), collapsing glomerulonephropathy, immune and inflammatory glomerulonephropathies, hypertensive hephrophathy, and age associated glomerulonephropathy.

The individual treated by a method embodied by the invention can, for instance, be a member of the bovine, porcine, ovine or equine families, a laboratory test animal such as a mouse, rat, rabbit, guinea pig, cat or dog, or a primate or human being. Typically, the mammal will be a human being.

Suitable pharmaceutically acceptable salts include acid and amino acid addition salts, base addition salts, esters and amides that are within a reasonable benefit/risk ratio, pharmacologically effective and appropriate for contact with animal tissues without undue toxicity, irritation or allergic response. Representative acid addition salts include hydrochloride, sulfate, bisulfate, maleate, fumarate, succinate, tartrate, tosylate, citrate, lactate, phosphate, oxalate and borate salts. Representative base addition salts include those derived from ammonium, potassium, sodium and quaternary ammonium hydroxides. The salts may include alkali metal and alkali earth cations such a sodium, calcium, magnesium and potassium, as well as ammonium and amine cations. The provision of such salts is well known to the skilled addressee. Suitable pharmaceutical salts are for example exemplified in S. M Berge et al, J. Pharmaceutical Sciences (1997), 66:1-19, the contents of which is incorporated herein in its entirety by cross-reference.

Prodrugs of compounds of the invention include those in which groups selected from carbonates, carbamates, amides and alkyl esters have been covalently linked to free amino, amido, hydroxy or carboxylic groups of the compounds. Suitable prodrugs also include phosphate derivatives such as acids, salts of acids, or esters, joined through a phosphorus-oxygen bond to a free hydroxl or other appropriate group. A prodrug can for example be inactive when administered but undergo in vivo modification into dynamin ring stabilizer as a result of cleavage or hydrolysis of bonds or other form of bond modification post administration. The prodrug form of the active compound can have greater cell membrane permeability than the active compound thereby enhancing potency of the active compound. A prodrug can also be designed to minimise premature in vivo hydrolysis of the prodrug external of the cell such that the cell membrane permeability characteristics of the prodrug are maintained for optimum availability to cells and for systemic use of the compound.

Esterified prodrugs may for instance be provided by stirring a compound embodied by the invention with an appropriate anhydride or acid chloride (in molar excess) in a pyridine/N,N-dimethylformamide (DMF) solution in the presence of a suitable catalyst such as dimethylaminopyridine (DMAP). In some cases, the solution may need to be refluxed to drive the reaction to completion. On completion of the reaction, the esterified product is purified by either recrystallization or by chromatography. Representative esters include $C_1$-$C_7$ alkyl, phenyl and phenyl($C_{1-6}$) alkyl esters. Preferred esters include methyl esters. Examples of suitable prodrug groups are shown in Table 3.

TABLE 3

Examples of prodrug groups

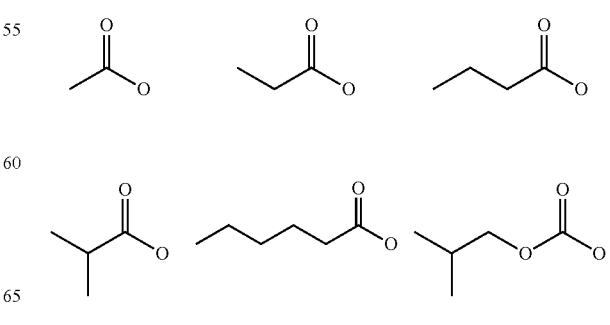

TABLE 3-continued

Examples of prodrug groups

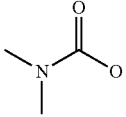

Scheme 3: Synthesis of prodrugs

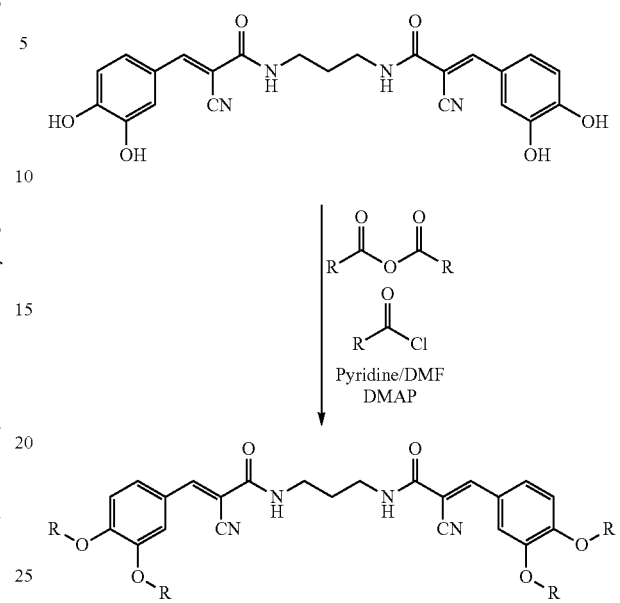

For instance, prodrugs of Bis-T-22 and analogues thereof were developed to increase cell membrane permeability characteristics and thereby increase potency in cells. A suitable reaction for providing prodrugs of dimeric tyrphostin compounds is illustrated in Scheme 3. Bis-T-22 is exemplified as the starting reagent. The dimeric tyrphostin compound is stirred with appropriate anhydride or acid chloride (in molar excess) in a pyridine/N,N-dimethylformamide (DMF) solution in the presence of an appropriate catalyst such as dimethylaminopyridine (DMAP). In some cases, the solution may need to be refluxed to drive the reaction to completion. On completion of the reaction, the esterified product is purified by either recrystallization or by chromatography. Particular dimeric benzylidenemalonitrile tyrphostin prodrugs developed are shown in Table 4 and Table 5.

TABLE 4

Prodrugs of bis-tyrphostin (Bis-T-22)

| Prodrug | R |
|---|---|
| TH-1 | CH$_3$ |
| TH-2 |  |
| TH-3 |  |
| TH-4 |  |
| TH-5 |  |
| TH-6 |  |
| TH-7 |  |
| TH-8 |  |

TABLE 4-continued
Prodrugs of bis-tyrphostin (Bis-T-22)
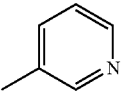
| Prodrug | R |
|---------|---|
| TH-9 | 3-pyridylmethyl |
TABLE 5
Further prodrug forms
| Prodrug | R | Mw |
|---------|---|-----|
| Pro-BisT | acetate | 616.59 |
| 80-1 | propionate | 672.68 |
| 80-2 | butyrate | 728.78 |
| 80-3 | isobutyrate | 728.78 |
| 80-4 | valerate | 841.00 |
| 80-5 | isobutyl carbonate | 964.04 |
| 80-6 | dimethylcarbamate | 723.74 |

TABLE 5-continued

Further prodrug forms

| Prodrug | R | Mw |
|---|---|---|
| 81-1 | nicotinoyloxy | 868.80 |
| 81-2 | N-methyl nicotinoyloxy | 928.942 |

The dynamin ring stabilizer can be administered to an individual in need of such treatment alone or be co-administered with one or more other therapeutic compounds or drugs conventionally used for treating or alleviating symptoms associated with proteinuric kidney disease. By "co-administered" is meant simultaneous administration of the drugs in the same formulation or in two different formulations by the same or different routes, or sequential administration by the same or different routes, where the drugs act in overlapping therapeutic windows.

The dynamin ring stabilizer will generally be formulated into a pharmaceutical composition comprising the stabilizer and a pharmaceutically acceptable carrier. Injectable solutions will typically be prepared by incorporating the stabilizer in the selected carrier prior to sterilizing the solution by filtration. For oral administration, the dynamin ring stabilizer can be formulated into any orally acceptable carrier deemed suitable. In particular, the dynamin ring stabilizer can be formulated with an inert diluent, an assimilable edible carrier or it may be enclosed in a hard or soft shell gelatin capsule. Moreover, the dynamin ring stabilizer can be provided in the form of ingestible tablets, buccal tablets, troches, capsules, elixirs, suspensions or syrups.

A pharmaceutical composition as described herein can also incorporate one or more preservatives such as parabens, chlorobutanol, phenol, and sorbic acid. In addition, prolonged absorption of the composition may be brought about by the inclusion of agents for delaying absorption such as aluminium monosterate. Tablets, troches, pills, capsules and like can also contain one or more of the following: a binder such as gum tragacanth, acacia, corn starch or gelatine, a disintegrating agent such as corn starch, potato starch or alginic acid, a lubricant, a sweetening agent such as sucrose, lactose or saccharin, a flavouring agent, and be provided with an enteric coating to facilitate passage through the acid environment of the stomach into the small intestine.

Pharmaceutically acceptable carriers include any suitable conventionally known physiologically acceptable solvents, dispersion media, isotonic preparations and solutions including for instance, physiological saline. Use of such ingredients and media for pharmaceutically active substances is well known. Except insofar as any conventional media or agent is incompatible with the mimetic, use thereof is expressly encompassed. It is particularly preferred to formulate compositions in dosage unit form for ease of administration and uniformity of dosage. A dosage unit form as used herein is to be taken to mean physically discrete units, each containing a predetermined quantity of the dynamin ring stabilizer calculated to produce a therapeutic or prophylactic effect. When the dosage unit form is a capsule, it can contain the active in a liquid carrier. Various other ingredients may be present as coatings or to otherwise modify the physical form of the dosage unit.

Pharmaceutical compositions embodied by the invention will generally contain at least about 0.1% by weight of the dynamin ring stabilizer up to about 80% w/w of the composition. The amount of the dynamin ring stabilizer in the composition will be such that a suitable effective dosage will be delivered to the individual taking into account the proposed mode of administration. Preferred oral compositions will contain between about 0.1 μg and 4000 mg of the stabilizer.

The dosage of the dynamin ring stabilizer will depend on a number of factors including whether it is to be administered for prophylactic or therapeutic use, the disease or condition for which the active is intended to be administered, the severity of the condition, the age of the individual, and related factors including weight and general health of the individual as may be determined in accordance with accepted medical principles. For instance, a low dosage may initially be given which is subsequently increased at each administration following evaluation of the individual's response. Similarly, frequency of administration can be determined in the same way that is, by continuously monitoring the individual's response between each dosage and if necessary, increasing the frequency of administration or alternatively, reducing the frequency of administration.

Typically, a dynamin ring stabilizer will be administered in accordance with a method embodied by the invention at a dosage up to about 50 mg/kg body weight and preferably, in a range of from about 1 mg/kg to about 30 mg/kg body weight.

Routes of administration include but are not limited to intravenously, intraperitonealy, by infusion, orally, rectally, and by implant. Suitable pharmaceutically acceptable carriers and formulations useful in compositions of the present invention may for instance be found in handbooks and texts well known to the skilled addressee, such as "Remington: The Science and Practice of Pharmacy (Mack Publishing Co., 1995)", the contents of which is incorporated herein in its entirety by reference.

The invention will be further described herein after with reference to non-limiting Examples.

Example 1

Dynamin Assembly Assays

1. Dynamin Self-Assembly Assay—Low Dynamin Concentration

The dynamin self-assembly assay was performed with native dynamin (40 nM) using the same Hepes column buffer (HCB—20 mM Hepes, 2 mM EGTA, 1 mM $MgCl_2$ 1 mM PMSF, 1 mM DTT, 20 µg/ml leupeptin, pH 7.4) as described previously (Warnock et al. 1996). However, all buffers also included 1% DMSO, which was the vehicle used for the test dynamin inhibitors. NaCl concentrations were varied from a stock in 200 mM NaCl. Dynamin was centrifuged at 100,000 g for 20 min, and the supernatants (S) and pellets (P) were collected, precipitated with trichloracetic acid, solubilised in SDS sample buffer and separated on SDS gels and dynamin I was detected by Western blotting using an in house sheep polyclonal α-dynamin I antibody.

2. High Dynamin Concentration Self-Assembly Assay—High Dynamin Concentration

This dynamin self-assembly assay was performed with native dynamin (5.2 µM) using the Hepes column buffer described above in Example 1.1, (with the addition of 1% DMSO as described above). Bis-T effects were measured by pre-incubating the dynamin with the indicated Bis-T concentrations for 10 min at room temperature (22° C.). NaCl concentrations were varied from a stock in 200 mM NaCl. After the incubation the tubes were transferred to a TLA120.2 rotor (Beckman) and centrifuged in a tabletop ultracentrifuge (Optima TLX, Beckman) at 100,000 g for 20 min, and the supernatants (S) and pellets (P) were collected, precipitated with trichloracetic acid, solubilised in SDS sample buffer and separated on SDS gels.

Example 2

Dynamin Ring Stabilizers are a Subgroup of Dynamin Inhibitors

Figure 1:
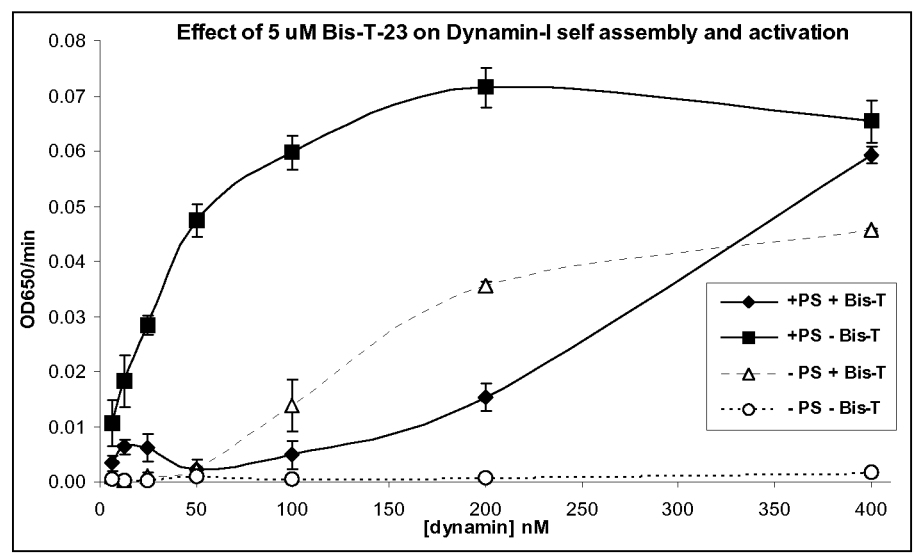
FIG. 1 is a graph showing that the dimeric benzylidenemalonitrile tyrphostin Bis-T-23 inhibits lipid-stimulated dynamin, but stimulates basal dynamin GTPase activity.

Among the various classes of dynamin inhibitors are subsets of dynamin ring stabilizers. Bis-T dimeric benzylidenemalonitrile tyrphostins potently inhibit helical dynamin GTPase activity and can stimulate the basal activity via promotion of ring formation in the absence of a template for dynamin helical assembly. FIG. 1 shows the in vitro GTPase activity of purified sheep brain dynamin (mostly this is dynamin I) at increasing dynamin concentrations, below those required for ring assembly. The filled symbols (solid lines) show that dynamin is stimulated by liposomes at all dynamin concentrations tested (forming a helix). 2-Cyano-N-{3-[2-cyano-3-(3,4,5-trihydroxyphenyl)-acryloylamino]-propyl}-3-(3,4,5-trihydroxyphenyl)-acrylamide (Bis-T-23) at 5 µM potently inhibits dynamin at all points (however at very high dynamin (400 nM), Bis-T-23 fails to inhibit, potentially because of the high dynamin concentration).

In contrast, in the absence of liposomes (where dynamin is unable to form helices) the results are strikingly opposite (FIG. 1, open symbols, dotted lines). Using dynamin concentrations below those necessary to form rings, Bis-T-23 potently stimulates dynamin activity. In contrast to helical dynamin which is inhibited at all dynamin concentrations, in the absence of liposomes Bis-T-23 does not activate or inhibit dynamin at low dynamin concentrations, but stimulates only at 100 nM or higher dynamin concentration (FIG. 1). This indicates that Bis-T-23 is neither an activator nor inhibitor of the basal GTPase activity of dynamin, but is affecting ring dynamin.

Figure 2:
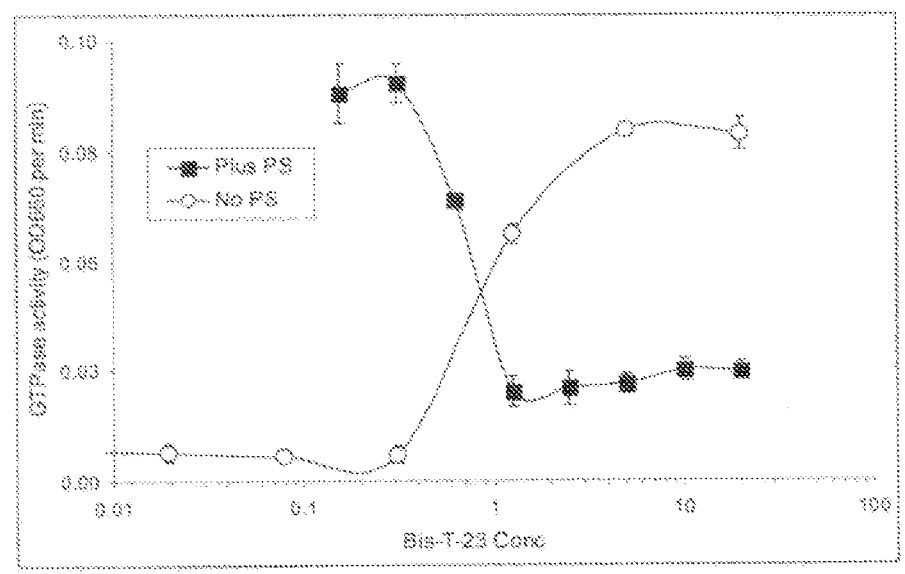
FIG. 2 is a graph showing inhibition and activation of dynamin occur at the same Bis-T-23 concentration.

The $IC_{50}$ for inhibition of PS-stimulated helical dynamin in this experiment is study 500 nM (FIG. 2). The concentration of Bis-T-23 causing 50% activation of basal dynamin activity ($EC_{50}$) was strikingly about the same value. This suggests the mechanism of ring stabilization and of inhibition may be related for this series of compounds.

Figure 3:
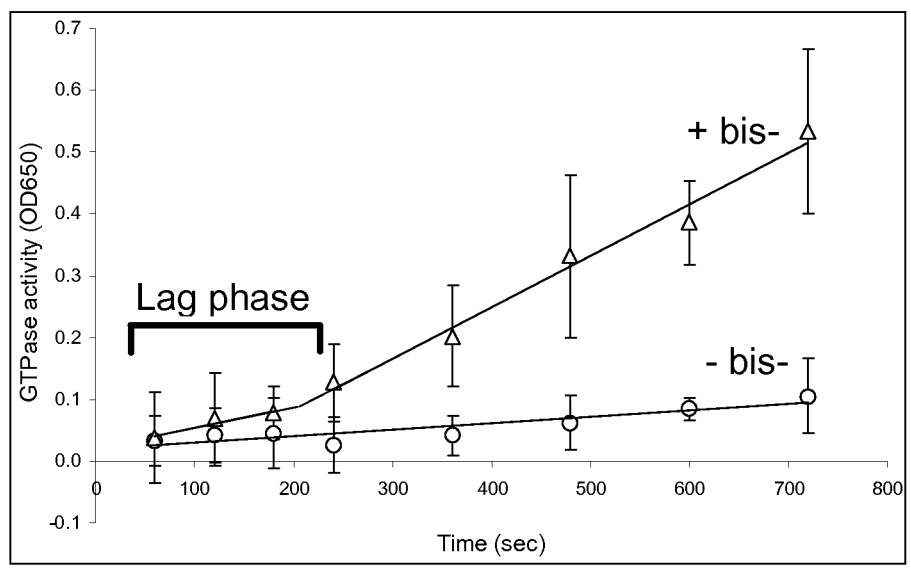
FIG. 3 is a graph showing Bis-T-23 (5 µM) stimulation of basal dynamin GTPase activity occurs after a "lag phase".

Next, a time course experiment of Bis-T-23 stimulation of dynamin GTPase (FIG. 3) was conducted. Using high dynamin concentrations (800 nM) and medium NaCl concentrations (30 mM), dynamin basal GTPase activity was linearly increased with time, since it did not assemble as rings in these conditions. In the presence of 5 µM Bis-T-23 dynamin activity was greatly increased after an initial "lag phase" of about 4 minutes. The lag phase is thought to indicate the time required for dynamin to assemble as rings. The results show that Bis-T-23 does not accelerate initial rates of dynamin ring assembly, suggesting it instead inhibits ring disassembly.

Figure 4:
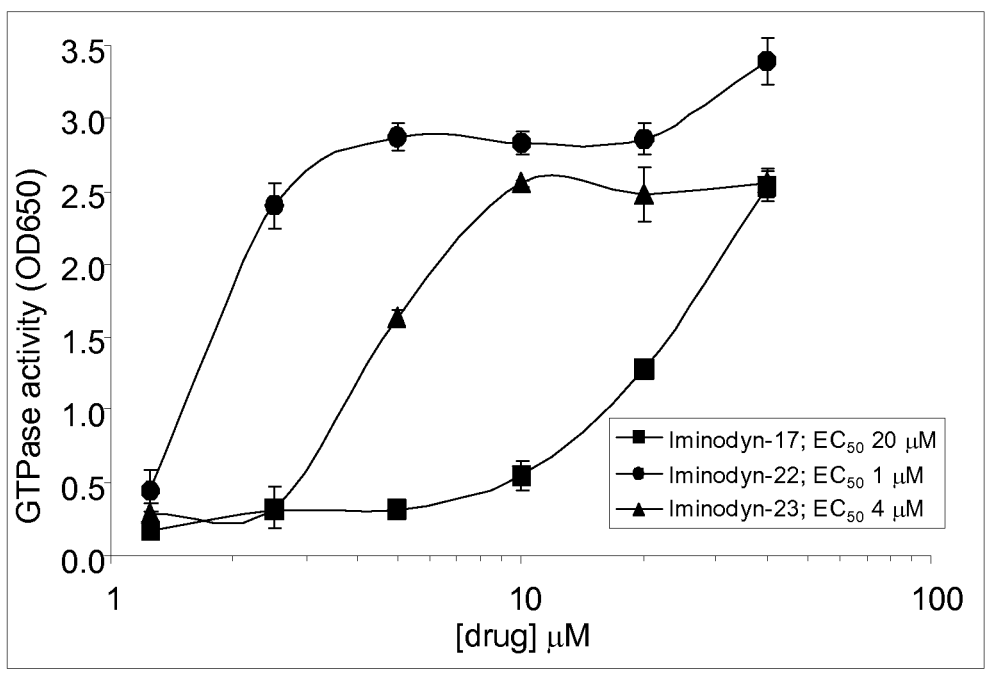
FIG. 4 is a graph showing the relative potency of three iminodyns on stimulating the basal GTPase activity of full length dynamin I (200 nM, no other known activators such as PS liposomes were present). The compounds were present at the indicated concentrations and the concentration causing half-maximal stimulation is shown as the $EC_{50}$.

When a series of potent iminodyn dynamin inhibitors were tested for ring stabilizer activity, a subset were found to be potent activators of basal dynamin GTPase activity (ie in the absence of PS; FIG. 4). Iminodyns-17, 22 and 23 had stimulation values ($EC_{50}$) from 1-20 µM, indicative of ring stabilizer activity.

There was little correlation between $IC_{50}$ for PS-stimulated dynamin and $EC_{50}$ for dynamin in the absence of PS. Therefore, only a subset of dynamin inhibitors are ring stabilizers and ring stabilizers cannot be recognised as simply potent inhibitors of PS-stimulated dynamin GTPase activity (Table 2). For example, iminodyns 17 and 22 are equipotent dynamin inhibitors yet are 30 fold different in ring stabilizer activity. Likewise, iminodyns 20 and 21 are similarly potent dynamin inhibitors yet iminodyn 20 exhibits no ring stabilizer activity (Table 2). Thus ring stabilizer activity can be identified by the ability to stimulate the activity of dynamin protein, in the absence of other stimulatory factors (such as PS liposomes, microtubules or nanotubes).

To verify that ring stabilizers require dynamin oligomerisation, a recombinant form of dynamin, called GG-2, which is dimeric yet is unable to self-associate into higher order oligomers (Chappie et al 2009) was tested. Ring stabilizers are unable to stimulate the basal activity of such constructs (FIG. 5).

The dynamin concentration-dependence of the activation effect of Bis-T-23 suggested it may be altering the in vitro formation of dynamin rings. A block in ring disassembly should be manifested as an accumulation of rings in vitro. Dynamin self-assembles into rings in the absence of any cofactors when the buffer ionic strength is decreased (Song et al. 2004). To determine whether Bis-T compounds regulate dynamin-dynamin interactions a well-established method of high speed centrifugation in decreasing amounts of NaCl to collect rings in the pellet (Warnock et al. 1996) was used. Higher concentrations of dynamin (520 nM) and dynamin was visualized by Coomassie staining on SDS gels (FIG. 6). As reported by others, dynamin is in the supernatant at ≥40 mM NaCl, but self-assembled at ≤20 mM NaCl and is found in the pellet. Bis-T-22 at 100 µM increased ring assembly at the intermediate salt concentrations (40, 60 nM) prior to its spontaneous assembly at lower salt. At a fixed 40 mM NaCl, Bis-T-22 promoted all dynamin to form rings at 300 µM concentrations. Therefore, under these conditions Bis-T-22 stabilized/promoted dynamin I self-assembly. Thus, it was concluded that there is a direct effect on dynamin-dynamin interactions, with the compound appearing to promote dynamin ring assembly and GTPase activity in vitro by virtue of preventing ring disassembly. Hence, GTPase active rings accumulate.

To directly demonstrate whether dynamin ring stabilizers prevent or retard the disassembly of dynamin rings a well established centrifugation assay was employed. Briefly, dynamin I was preassembled as a helix in the presence of PS liposomes for 30 min, after which the dynamin ring stabilizer Bis-T-23 or non-dynamin ring stabilizer dynole 34-2 (see Example 4) were added. The samples were then centrigued in a microfuge for 10 min to collect supernatans (Sup) or pellets. In this assay, helical dynamin is found primarily in the pellet. However, the addition of either NaCl (150 mM) or Mg/GTP (1 mM) is known to disassemble dynamin and it is found primarily in the supernatant (see FIG. 7). Bis-T-23 was found to reduce the disassembly of helical dynamin, while dynole 34-2 did not (FIG. 7). This shows that the mechanism whereby Bis-T acts as a dynamin ring stabilizer is, or includes, retarding dynamin ring or helix disassembly. This unique mechanism of action explains why dynamin ring stabilizers can stimulate basal GTPase while inhibiting helical dynamin GTPase activity at the same time.

Example 3

Bis-T-23 Produces Inflexible Dynamin Rings In Vitro

A characteristic of helical dynamin is that the helix is a highly flexible structure. Upon GTP hydrolysis it is able to rapidly reduce its diameter (constriction) while also expanding in length (helical expansion) (Stowell et al. 1999; Chen et al. 2004; Roux et al. 2006). This is thought to be a potential mechanism utilized for the fission of the necks of newly budded endocytic vesicles in cells (Roux et al. 2006). The highly flexible nature of helical dynamin was confirmed by EM analysis of dynamin bound to phosphatidylserine liposomes in the absence of GTP or GDP (FIG. 8). Dynamin mixed with PS liposomes formed a helix with specific characteristics (FIGS. 8A and C): the individual loops of the helix were highly varied in diameter, formed at different angles relative to the underlying lipid, and the spacing between loops was highly variable. In contrast, 5 µM Bis-T-23 drastically altered the helical shape (FIGS. 8B and D). Notably the individual loops of the helix were highly uniform in diameter, formed at constant angles relative to the underlying lipid, and the spacing between loops was highly constant. Bis-T-23 bound dynamin appeared similar to previous reports of GTPγS-bound dynamin on lipid nanotubes (Stowell et al. 1999). This indicates that Bis-T-23 can lock dynamin loops into an inflexible and uniform diameter, akin to the GTP-bound state, by preventing ring disassembly. The effect is particularly noticeable at the ends of each helical tube, which are "tapered" in the absence of Bis-T-23, yet "blunt" in its presence (FIG. 8C-D), demonstrating the inflexibility of Bis-T-23 affected loops.

The electron microscope (EM) results revealed a common mechanism for both inhibition and activation of dynamin GTPase. It was concluded that the super-elevated GTPase activity of helical dynamin is inhibited by Bis-T-23 because the drug renders the loops of the helix inflexible. In the absence of PS liposomes, the activity of the individual dynamin rings induced by the presence of Bis-T-23 is stimulated due to the same accumulation of uniformly sized inflexible rings. Thus, it was concluded that Bis-T-23 prevents the dynamin rapid disassembly that would normally be driven by GTP hydrolysis, which drives dynamin disassembly in vitro.

Next, the effect of a ring stabilizer Bis-T-23 on the formation of dynamin rings in the absence of a template like PS liposomes was examined. At high concentrations in vitro, dynamin is well known to self-assemble into rings that are detectable by EM (Hinshaw and Schmid, 1995). Such self assembly requires high dynamin concentrations typically in the order of 500-1000 nM and is not observed at lower dynamin concentrations. Specifically, the effect of Bis-T-23 (5.4 µM) on 200 nM dynamin in the absence of template was tested, which is well below the concentration threshold for self-assembly. As expected, dynamin did not self-assemble to appreciable levels at this concentration (FIG. 9A). However in the presence of Bis-T-23, dynamin showed an unanticipated massive increase in self assembly (FIG. 9A). High power images confirmed that the electron dense structures are bona fide dynamin rings (FIG. 9B). Quantitative analysis of about 2000 dynamin rings showed a massive increase in ring formation induced by Bis-T-23 (FIG. 9C). These results confirm that Bis-T-23 promotes the accumulation of dynamin rings by either inducing their formation or by preventing their disassembly. The findings with basal dynamin are completely unexpected for a dynamin inhibitor and are indicative of the ring stabilizer activity.

Example 4

Bis-T-22 Produces Inflexible Dynamin Rings in Cells

This Example shows that a dynamin ring stabilizer is able to promote dynamin ring formation in cells and prevent or retard their disassembly. When vesicles are endocytosed via the clathrin-dependent pathway, they are well known to be internalised as omega shaped figures close to the plasma membrane with partially constricted and short necks. These can be detected by transmission electron microscopy (EM) at a low frequency. Treatment of cells for 10-30 minutes with a classical dynamin inhibitor such as dynasore causes a massive accumulation of clathrin coated pits at the plasma membrane of cells without promotion of dynamin rings (Macia et al, 2006). Other dynamin inhibitors like MiTMAB (Quan et al, 2007) or dynole 34-2 do not induce any accumulation of coated pits, presumably because they at least partly act at the lipid surface to prevent their initial formation and are inhibitors without ring stabilizer characteristics. In contrast to these observations, a dynamin ring stabilizer causes accumulation of clathrin coated pits in cells with two distinctive features: the vesicle necks are highly elongated and are encircled by electron dense rings. Human lymphoblasts (which express dynamin II) were treated with dynasore, MiTMAB (not shown) or Bis-T-22 for 30 min and prepared for EM analysis. While dynasore and MiTMAB produced the expected outcomes reported previously, Bis-T-22 elicited a massive accumulation in all cells of clathrin coated pits with highly elongated necks and which were encircled by rings or spirals (FIG. 10A). Similarly, when rat brain synaptosomes (isolated nerve terminals, which primarily express dynamin I) were treated with Bis-T-22 for 30 min and depolarised with KCl to evoke endocytosis, trapped endocytic pits were detected that were encircled by a single electron dense ring (FIG. 10B lower 3 panels). No rings or trapped vesicles were detected when the synaptosomes were unstimulated (FIG. 10B top). This mimics the in vitro observations on purified dynamin I described earlier which forms single rings (FIG. 9).

These observations illustrate that ring stabilizers have the ability to promote and stabilise rings at sites of trapped endocytosis in distinct cellular types. This characteristic is not found with dynamin inhibitors that are not dynamin ring stabilizers, supporting that dynamin ring stabilization is a novel action of ring stabilizer compounds which can occur in the context of live cells and is not restricted to in vitro conditions with the purified protein.

Example 5

Not all Dynamin Inhibitors are Dynamin Ring Stabilizers

A new series of potent dynamin GTPase inhibitors based on the structure of dynasore (Macia et al. 2006) was designed. These compounds were called dyngo's. The most active dyngo analogue is dyngo-4a, with an $IC_{50}$ for PS-stimulated dynamin of 300 nM, in comparison with dynasore (dyngo-7a) $IC_{50}$ of 14 µM. The structure of the dyngos resembles a monomeric form of the Bis-T and also monomeric tyrphostins. However, it was found that the dyngos, and especially dynasore, strongly bind to the detergent Tween-80 which is a normal component of assays to screen for dynamin inhibitors (Quan and Robinson 2005). Upon performing the basal GTPase assay in the present studies in the absence of Tween-80, it was found that both the dyngos and dynasore stimulated basal dynamin GTPase activity to similar extents as Bis-T-23 (FIG. 10A). This shows that basal dynamin GTPase activation (i.e., dynamin ring activation) is not restricted to Bis-T tyrphostins nor iminodyns.

Another potent dynamin inhibitor series in a novel chemical class are the "dynole" series of compounds, which are indole-based inhibitors as described in International Patent Application No. PCT/IB2008/002387 (WO 2009/034464) (see also Hill et al. 2009). The most potent dynole developed to date is dynole 34-2 (2-cyano-3-(1-(2-(dimethylamino)-ethyl)-1H-indol-3-yl)-N-octylacrylamide) with an $IC_{50}$ for PS-stimulated dynamin of 1 µM. Dynole 34-2 failed to stimulate the basal activity of dynamin (FIG. 11A). Hence, it is not a dynamin ring disassembly inhibitor (i.e., not a dynamin ring stabilizer).

Next, a range of potent Bis-T analogues were tested in the standard GTPase assay employed in the presence of Tween-80. Four of the most potent dynamin inhibitors (Hill et al. 2005) were also found to be dynamin ring stabilizers since they increased basal activity (FIG. 11B). Dyngo-4a was also effective, although dynasore failed to stimulate basal GTPase activity under these conditions (due to its non-specific Tween-80 binding). Importantly, several dynamin inhibitors in the MiTMAB series (which target the PH domain, Quan et al 2007) or dynole series (which target an allosteric site in the GTPase domain, Hill et al. 2009) failed to stimulate basal dynamin GTPase activity (FIG. 11B). Therefore, dynamin inhibitors with distinct mechanisms of action on dynamin do not all increase the basal dynamin GTPase activity (i.e., they are not all dynamin ring stabilizers). This indicates that ring stabilizers represent a distinct class of dynamin modulator, not specifically connected to their ability or not to inhibit template-stimulated dynamin GTPase activity in vitro.

In summary, a variety of dynamin ring stabilizers from a number of distinct chemical classes were identified herein by their ability to stimulate the basal activity of full length dynamin. The mechanism of stimulation was explained since these compounds specifically stabilize dynamin self-assembly into single rings (thereby stimulating the basal rate of GTP hydrolysis), most likely by inhibiting dynamin disassembly. Not all the dynamin ring stabilizers were potent inhibitors of helical dynamin GTPase activity. Importantly, dynamin self-assembly into rings has a specific and selective effect on the actin cytoskeleton (see below), and these compounds are able to stabilize or prolong the function of dynamin rings in the actin cytoskeleton.

Example 6

Actin Stimulates Dynamin Ring Assembly In Vitro

In the present study, it was found that the formation of rings by dynamin is essential for increasing the actin cytoskeleton in podocytes, and direct interactions between dynamin and filamentous actin (F-actin) were identified. In particular, an unrecognized actin binding site in dynamin was identified that binds along actin filaments and aligns them into bundles. F-actin, and in particular, short filaments capped on their barbed ends by gelsolin (Gsn), promote dynamin ring formation and stimulate its GTPase activity. This interaction, in turn, dissociates gelsolin from the barbed filament ends and promotes filament elongation. The reciprocal interplay between dynamin and Gsn-capped filaments can thus influence the architecture and dynamics of actin. Dynamin mutants defective in actin-binding in vitro have impaired oligomerization in cells and reduce actin stress fiber assembly, and altered cortical actin cytoskeletal behavior in cultured podocytes. In contrast, a dynamin mutant with increased actin affinity has an increased propensity to oligomerize in the cytoplasm and stimulates stress fiber assembly in the perinuclear region of the cell. These findings suggest a complex interplay between dynamin's GTPase cycle and the global organization of the actin cytoskeleton in podocytes.

Example 7

Dynamin Binds F-Actin

To determine whether dynamin affects the actin cytoskeleton, the question of whether dynamin might directly bind filamentous actin (F-actin) was tested. In particular, an actin co-sedimentation assay was performed in which F-actin sediments under high-speed centrifugation. If dynamin interacts with F-actin it would be expected to co-sediment, and thus be present in the pellet fraction. In the presence of F-actin, but not in its absence, the majority of dynamin was found in the pellet (FIG. 12, lanes 2 and 14). Dynamin-actin interactions did not require the presence of GTP, indicating they did not require dynamin oligomerization. Moreover, dynamin binding to F-actin was observed in the presence of GTPγS (FIG. 12, lane 6), indicating dynamin oligomerization was not inhibitory for binding. The Kd of dynamin for actin was approximately 0.4 µM, which is similar to the affinities of other actin binding proteins such as α-actinin 4 for actin (Weins et al. 2005).

Example 8

The Actin Binding Domain of Dynamin is in the Dynamin Middle Domain

Next, the actin binding site was mapped to a region between amino acids 399 and 444 amino acids of dynamin II (dyn2) (FIG. 13). As predicted for an actin binding domain (Van et al. 1996), this region contains several positively charged amino acids conserved in all dynamin gene products from yeast to mammals. It is also alternatively spliced within different mammalian dynamin isoforms (called variant a and b in dynamins I and II) (see FIG. 13, SEQ ID No. 1-4). Site-directed mutagenesis was performed on conserved, charged residues within this actin binding domain to generate the putative 'loss of function' mutants, dynK/E (SEQ ID No. 9) and dynK/A (SEQ ID No. 10), and a putative 'gain of function' mutant, dynE/K (SEQ ID No. 11) (FIG. 13). The affinities of dynK/E and dynK/A for actin were found to be reduced (Kd of 1.7 and 2.8 µM, respectively), whereas the affinity of dynE/K for actin was increased (Kd=0.03 µM) (FIG. 14). All three mutant proteins had wild-type kinetic properties with respect to the basal and stimulated rate of GTP hydrolysis, indicating proper folding.

Example 9

Dynamin-Actin Interactions are Involved in the Actin Cytoskeleton of Podocytes To determine the role of dynamin-actin interactions in actin organization, the consequences for podocyte morphology of expressing dynamin mutants with altered affinity for F-actin was examined. In fully differentiated mouse podocytes, the actin cytoskeleton is organized in parallel bundles of actin-myosin contractile stress fibers in the cell body and a cortical network of short, branched actin filaments located beneath the plasma membrane that drives formation of lamellipodia and filopodia. Expression of dynK44A, a dynamin mutant that cannot bind GTP, abolished stress fibers within the cell body and generated a thick, hyper-bundled actin network in the vicinity of the plasma membrane, causing a polygonal cellular shape (Sever et al. 2007). In the present study it was found that expression of dynK44A abolished formation of lamellipodia and filopodia (FIG. 15B). Expression of the 'loss of function' mutant dynK/E resulted in reduction of stress fibers and dramatic changes in cell shape (FIG. 15C). In contrast, expression of the 'gain of function' dynE/K caused a clear increase in stress fibers within the cell body (FIG. 15D). A similar increase in stress fibers was observed in cells expressing dynR725A (FIG. 15E), the mutant that lives longer in the assembled GTP-bound state.

Example 10

Dynamin Rings Cross-Link F-Actin into Tight Bundles

To evaluate the effects of dynamin on the structure of actin filaments, F-actin was examined using negative staining and electron microcopy (EM). Dynamin oligomerized into rings by the addition of GTPγS (a non-hydrolysable GTP analog that promotes its ring formation) and crosslinked actin filaments into tight bundles (FIG. 16). The filament-to-filament spacing in these bundles was 17-20 nm, less than the diameter of a dynamin ring (~50 nm). Thus, these findings suggest that in the absence of other actin binding proteins dynamin rings can form actin bundles composed of parallel filaments with well-defined spacing. Such parallel actin filaments occur in stress fibers and filopodia. This is believed to be the first report of a biological function for the ring form of dynamin.

Example 11

Dynamin Rings Displace Gelsolin from Barbed Filament Ends

Next, the question of whether dynamin can expose the barbed ends of gelsolin (Gsn) capped F-actin was tested. Actin was polymerized in the presence of gelsolin at the indicated ratios (1G:A200 or 1G:A1000) (FIG. 17). Under these conditions, gelsolin caps >99% of the barbed end. The filament length is defined by the Gsn:actin ratio (~0.5 µm or 2.7 µm, respectively) and the extent of actin polymerization is controlled by the critical concentration of pointed filament ends which is ~0.6 µM. The actin solution was then diluted to 0.33 µM in the presence or absence of dynamin. Under these conditions, actin can only repolymerize if barbed ends become available. Addition of dynamin induced actin polymerization, but only in the presence of GTPγS (FIG. 17, compare the diamonds and circles with the squares). This is consistent with dynamin rings having the capacity to displace gelsolin from the barbed filament ends either directly or by altering F-actin structure at its barbed ends. Overall, the data establish an interconnection between F-actin dynamics and dynamin oligomerization. In particular, short, gelsolin capped actin filaments promote dynamin ring formation, which in turn dissociates gelsolin from the barbed ends and allows filament elongation.

Example 12

Bis-T-23 Stimulates Formation of Dynamin Rings

Both dynR725A and dynE/K are predicted to live longer in dynamin ring formation (Sever et al. 2007). DynR725A was previously reported to rescue proteinuria in an LPS model by oligomerizing into the rings and thus avoiding cleavage by the protease cathepsin L (CatL) (Sever et al. 2007). The expression of dynR725A is sufficient to reduce proteinuria in a mouse model of nephrotic syndrome (Sever et al. 2007).

The question of whether Bis-T-22 and Bis-T-23 might activate wild type ring dynamin and phenocopy the dynR725A phenotype was tested. Bis-T-23 increased the rate of basal dynamin GTP hydrolysis to a similar level to addition of Gsn-F-actin complexes (FIG. 18). Thus, both Bis-T-23 and Gsn-F-actin complexes promote dynamin oligomerization into rings. When both reagents were simultaneously present, there was additional stimulation of dynamin's GTPase activity (FIG. 18). Together, these data suggest that Bis-T-23 does not compete for F-actin binding by dynamin, and that both components act additively or synergistically with respect to dynamin oligomerization.

Example 13

Bis-T-23 Stimulates Focal Adhesions and Stress Fibers in Cultured Podocytes To determine if the in vitro action of the dynamin ring stabilizers also occurs in cells, the effect of Bis-T-23 on the actin cytoskeleton in cultured mouse podocytes was tested (FIG. 19). 10 min after addition of Bis-T-23 there was a dramatic increase in well-defined stress fibers (FIG. 19B-D).

This was associated with a dramatic increase in the number of focal adhesions (paxillin staining in FIG. 19B). While Bis-T-23 inhibits endocytosis (not shown), the actin cytoskeleton is profoundly different compared to cells expressing dynK44A (loss of stress fibers and increase in hyper bundled actin filaments). Thus, the observed increase in stress fibers is unlikely due to inhibition of endocytosis.

These results show that dynamin rings have a role in the formation of stress fibers and focal adhesions in cultured podocytes, and that dynamin ring stabilizer molecules such as Bis-T may inhibit or reverse proteinuria by restoring functional FP due to actin reorganization.

Example 14

Inhibition of Proteinuria in Animal Models

To demonstrate the effectiveness of a ring stabilizer in vivo, two different mouse models of kidney disease were utilised, a genetic model and an acute toxicity model. Mice expressing a 'gain of function' mutation in the ACTN4 gene encoding for α-actinin 4 has been fully characterized (Kaplan et al. 2000; Henderson et al. 2008; Yao et al. 2004). These animals develop FP effacement and proteinuria due to "hyper bundling" activity of α-actinin 4 mutant that induces aggregation of stress fibers. Proteinuria develops at 4-6 weeks of age. The animals used in the present study were obtained from Dr. Martin Pollak, Brigham and Women's Hospital, Boston, Mass., USA. Proteinuric phenotype was confirmed by determination of urinary albumin and creatinine using mouse Albumin-specific ELISA and Creatinine Companion assay kits (Exocell and Bethyl Laboratories) following the manufacturer's protocols. The control animal was a littermate. Bis-T-23 was dissolved in 100% DMSO to make a 10 µg/µl stock solution, of which 5 µl was diluted in 200 µl of 1×PBS, and this was injected intraperitoneally (IP) into the test animal (166 µg/100 g body weight) at time 0 hr. Protein levels in the urine were measured every 2 hours post injection. The results are shown in FIG. 20. As can be seen, a decrease in proteinuria to wild-type levels was obtained up to 6 hours after administration of the Bis-T-23.

A second model of acute proteinuria was then employed to test the ability of a dynamin ring stabilizer to ameliorate proteinuria in a reversible model of proteinuric kidney disease. LPS-induced proteinuria was utilized as previously described (Sever et al., 2007). Briefly, four week old female BALB/c mice were injected twice intraperitoneally (IP) with 200 µg of ultrapure LPS diluted in phosphate-buffered saline at a concentration of 1 mg/ml. Proteinuria developed within 48 h (FIG. 20, 2×LPS). Bis-T-23 was dissolved in DMSO to the appropriate concentrations and 300 µg per 100 g body weight was delivered by IP injection, and DMSO was used as a vehicle control. The level of protein in the urine was determined by using mouse Albumin-specific ELISA kit according to manufacturer's protocol (Bethyl Laboratories). Administration of the Bis-T-23 partially rescued proteinuria from 2-6 h after injection (FIG. 21). Its ability to rescue proteinuria was reduced 8 h after injection. These results show that a ring stabilizer can ameliorate proteinuria in a mouse model of proteinuric kidney disease.

Although a number of embodiments have been described, it will be appreciated by persons skilled in the art that numerous variations and/or modifications may be made without departing from the spirit or scope of the invention as broadly described. The present embodiments are, therefore, to be considered in all respects as illustrative and not restrictive.

LITERATURE REFERENCES

Asanuma K., Kim K., Oh J., Giardino L., Chabanis S., Faul C., Reiser J. and Mundel P. (2005) Synaptopodin regulates the actin-bundling activity of alpha-actinin in an isoform-specific manner. J. Clin. Invest. 115, 1188-1198.

Asanuma K., Yanagida-Asanuma E., Faul C., Tomino Y., Kim K. and Mundel P. (2006) Synaptopodin orchestrates actin organization and cell motility via regulation of RhoA signalling. Nat. Cell Biol. 8, 485-491.

Chappie J. S., Acharya S., Liu Y. W., Leonard M., Pucadyil T. J. and Schmid S. L. (2009) An intramolecular signaling element that modulates dynamin function in vitro and in vivo. Mol. Biol. Cell 20, 3561-3571.

Chen Y. J., Zhang P., Egelman E. H. and Hinshaw J. E. (2004) The stalk region of dynamin drives the constriction of dynamin tubes. Nat. Struct. Mol. Biol. 11, 574-575.

Chao W-T., and Kunz J. (2009). Focal adhesion disassembly requires clathrin-dependent endocytosis of integrins. FEBS Lett. 583, 1337-1343.

Cousin M. A. and Robinson P. J. (2001) The dephosphins: Dephosphorylation by calcineurin triggers synaptic vesicle endocytosis. Trends Neurosci. 24, 659-665.

Faul C., Asanuma K., Yanagida-Asanuma E., Kim K. and Mundel P. (2007) Actin up: regulation of podocyte structure and function by components of the actin cytoskeleton. Trends Cell Biol. 17, 428-437.

Henderson J. M., Al-Waheeb S., Weins A., Dandapani S. V. and Pollak M. R. (2008) Mice with altered alpha-actinin-4 expression have distinct morphologic patterns of glomerular disease. Kidney Int. 73, 741-750.

Hill T. A., Gordon C. P., McGeachie A. B., Venn-Brown B., Odell L. R., Chau N., Quan A., Mariana A., Sakoff J., Chircop M., Robinson P. J. and McCluskey A. (2009) Inhibition of dynamin mediated endocytosis by the dynoles-synthesis and functional activity of a family of indoles. J. Med. Chem. Accepted Feb. 13, 2009.

Hill T. A., Odell L. R., Edwards J. K., Graham M. E., McGeachie A. B., Rusak J., Quan A., Abagyan R., Scott J. L., Robinson P. J. and McCluskey A. (2005) Small molecule inhibitors of dynamin I GTPase activity: Development of dimeric tyrphostins. J. Med. Chem. 48, 7781-7788.

Hill T. A., Odell L. R., Quan A., Abagyan R., Ferguson G., Robinson P. J. and McCluskey A. (2004) Long chain amines and long chain ammonium salts as novel inhibitors of dynamin GTPase activity. Bioorg. Med. Chem. Lett. 14, 3275-3278.

Hill T. A., Mariana A., Gordon C. P., Odell L. R., McGeachie A. B., Chau N., Daniel J. A., Gorgani N. N., Robinson P. J. and McCluskey A. (2010) Iminochromene inhibitors of dynamin I & II GTPase activity and endocytosis. J. Med. Chem. In press DOI: 10.1021/jm100119c. Published online http://pubs.acs.org/doi/full/10.1021/jm100119c Hinshaw J. E. and Schmid S. L. (1995) Dynamin self-assembles into rings suggesting a mechanism for coated vesicle budding. Nature 374, 190-192.

Ichimura K., Kurihara H. and Sakai T. (2003) Actin filament organization of foot processes in rat podocytes. J. Histochem. Cytochem. 51, 1589-1600.

Jones N., Blasutig I. M., Eremina V., Ruston J. M., Bladt F., Li H., Huang H., Larose L., Li S. S., Takano T., Quaggin S. E. and Pawson T. (2006) Nck adaptor proteins link nephrin to the actin cytoskeleton of kidney podocytes. Nature 440, 818-823.

Lima L. M. and Barreiro, E. J. (2005) Bioisosterism: A useful strategy for molecular modification and drug design. Curr. Med. Chem. 12, 23-49.

Kaplan J. M., Kim S. H., North K. N., Rennke H., Correia L. A., Tong H. Q., Mathis B. J., Rodriguez-Perez J. C., Allen P. G., Beggs A. H. and Pollak M. R. (2000) Mutations in ACTN4, encoding alpha-actinin-4, cause familial focal segmental glomerulosclerosis. Nat. Genet. 24, 251-256.

Macia E., Ehrlich M., Massol R., Boucrot E., Brunner C. and Kirchhausen T. (2006) Dynasore, a cell-permeable inhibitor of dynamin. Dev Cell 10, 839-850.

Moeller M. J. and Holzman L. B. (2006) Imaging podocyte dynamics. Nephron Exp Nephrol 103, e69-e74.

Moeller M. J., Soofi A., Braun G. S., Li X., Watzl C., Kriz W. and Holzman L. B. (2004) Protocadherin FAT1 binds Ena/VASP proteins and is necessary for actin dynamics and cell polarization. EMBO J. 23, 3769-3779.

Muhlberg A. B., Warnock D. E. and Schmid S. L. (1997) Domain structure and intramolecular regulation of dynamin GTPase. EMBO J. 16, 6676-6683.

Mundel P., Reiser J., Zuniga Mejia B. A., Pavenstadt H., Davidson G. R., Kriz W. and Zeller R. (1997) Rearrangements of the cytoskeleton and cell contacts induce process formation during differentiation of conditionally immortalized mouse podocyte cell lines. Exp. Cell Res. 236, 248-258.

Odell L. R., Chau N., Mariana A., Graham M. E., Robinson P. J. and McCluskey A. (2009) Azido and diazarinyl analogues of Bis-Tyrphostin as asymmetrical inhibitors of dynamin GTPase. Chem. MedChem In press, accepted 10 Mar. 2009.

Orth J. D. and McNiven M. A. (2003) Dynamin at the actin-membrane interface. Curr. Opin. Cell Biol. 15, 31-39.

Quan A., McGeachie A. B., Keating D. J., van Dam E. M., Rusak J., Chau N., Malladi C. S., Chen C., McCluskey A., Cousin M. A. and Robinson P. J. (2007) MiTMAB is a surface-active dynamin inhibitor that blocks endocytosis mediated by dynamin I or dynamin II. Mol. Pharmacol. 72, 1425-1439.

Quan A. and Robinson P. J. (2005) Rapid purification of native dynamin I and colorimetric GTPase assay. Methods Enzymol. 404 (Ch 49), 556-569.

Reiser J., Oh J., Shirato I., Asanuma K., Hug A., Mundel T. M., Honey K., Ishidoh K., Kominami E., Kreidberg J. A., Tomino Y. and Mundel P. (2004) Podocyte migration during nephrotic syndrome requires a coordinated interplay between cathepsin L and alpha3 integrin. J. Biol. Chem. 279, 34827-34832.

Roux A., Uyhazi K., Frost A. and De Camilli P. (2006) GTP-dependent twisting of dynamin implicates constriction and tension in membrane fission. Nature 441, 528-531.

Saleem M. A., O'Hare M. J., Reiser J., Coward R. J., Inward C. D., Farren T., Xing C. Y., Ni L., Mathieson P. W. and Mundel P. (2002) A conditionally immortalized human podocyte cell line demonstrating nephrin and podocin expression. J Am Soc Nephrol 13, 630-638.

Schafer D. A. (2004) Regulating actin dynamics at membranes: a focus on dynamin. Traffic 5, 463-469.

Sever S., Altintas M. M., Nankoe S. R., Moller C. C., Ko D., Wei C., Henderson J., del Re E. C., Hsing L., Erickson A., Cohen C. D., Kretzler M., Kerjaschki D., Rudensky A., Nikolic B. and Reiser J. (2007) Proteolytic processing of dynamin by cytoplasmic cathepsin L is a mechanism for proteinuric kidney disease. J. Clin. Invest. 117, 2095-2104.

Sever S., Damke H. and Schmid S. L. (2000a) Dynamin:GTP controls the formation of constricted coated pits, the rate limiting step in clathrin-mediated endocytosis. J. Cell Biol. 150, 1137-1148.

Sever S., Damke H. and Schmid S. L. (2000b) Garrotes, springs, ratchets, and whips: Putting dynamin models to the test. Traffic 1, 385-392.

Sever S., Muhlberg A. B. and Schmid S. L. (1999) Impairment of dynamin's GAP domain stimulates receptor-mediated endocytosis. Nature 398, 481-486.

Sever S., Skoch J., Newmyer S., Ramachandran R., Ko D., McKee M., Bouley R., Ausiello D., Hyman B. T. and Bacskai B. J. (2006) Physical and functional connection between auxilin and dynamin during endocytosis. EMBO J. 25, 4163-4174.

Song B. D., Leonard M. and Schmid S. L. (2004) Dynamin GTPase domain mutants that differentially affect GTP binding, GTP hydrolysis and clathrin-mediated endocytosis. J. Biol. Chem. 279, 40431-40436.

Stowell M. H., Marks B., Wigge P. and McMahon H. T. (1999) Nucleotide-dependent conformational changes in dynamin: evidence for a mechanochemical molecular spring. Nat. Cell Biol. 1, 27-32.

Susztak K. and Bottinger E. P. (2006) Diabetic nephropathy: a frontier for personalized medicine. J Am Soc Nephrol 17, 361-367.

Tryggvason K., Patrakka J. and Wartiovaara J. (2006) Hereditary proteinuria syndromes and mechanisms of proteinuria. N. Engl. J. Med. 354, 1387-1401.

Van T. M., Dewitte D., Goethals M., Carlier M. F., Vandekerckhove J. and Ampe C. (1996) The actin binding site of thymosin beta 4 mapped by mutational analysis. EMBO J. 15, 201-210.

Warnock D. E., Hinshaw J. E. and Schmid S. L. (1996) Dynamin self-assembly stimulates its GTPase activity. J. Biol. Chem. 271, 22310-22314.

Weins A., Kenlan P., Herbert S., Le T. C., Villegas I., Kaplan B. S., Appel G. B. and Pollak M. R. (2005) Mutational and biological analysis of alpha-actinin-4 in focal segmental glomerulosclerosis. J Am Soc Nephrol 16, 3694-3701.

Yao J., Le T. C., Kos C. H., Henderson J. M., Allen P. G., Denker B. M. and Pollak M. R. (2004) Alpha-actinin-4-mediated FSGS: an inherited kidney disease caused by an aggregated and rapidly degraded cytoskeletal protein. PLoS Biol 2, e167.

Zhang J., Lawrance G. A., Chau N., Robinson P. J. and McCluskey A. (2008) From Spanish fly to room temperature ionic liquids (RTILs): Synthesis, thermal stability and inhibition of dynamin 1 GTPase by a novel class of RTILs. New Journal of Chemistry 32, 28-36.

The invention claimed is:

1. A method for prophylaxis or treatment of a kidney disease or condition characterized by proteinuria, comprising administering to an individual in need thereof an effective amount of at least one dynamin ring stabilizer for maintaining and/or inducing actin cytoskeleton formation, or prodrug or pharmaceutically acceptable salt of the dynamin ring stabilizer.

2. A method according to claim 1 wherein the dynamin ring stabilizer is a helical dynamin GTPase inhibitor.

3. A method according to claim 1 wherein the dynamin ring stabilizer is not an inhibitor of dynamin GTPase activity.

4. A method according claim 1 wherein the dynamin ring stabilizer is a compound that promotes formation of dynamin rings.

5. A method according to claim 1 wherein the dynamin ring stabilizer is a compound that inhibits dynamin ring disassembly.

6. A method according to claim 1 wherein the dynamin ring stabilizer is selected from the group consisting of helical dynamin GTPase inhibitors, dimeric tyrphostins, dimeric benzylidenemalonitrile tyrphostins, iminochromenes, monomeric tyrphostins, and 3-substituted naphthalene-2-carboxylic acid (benzylidene) hydrazides.

7. A method according to claim 1 wherein the kidney disease or condition is selected from the group consisting of nephrotic syndrome, chronic kidney disease, glomerular disease, glomerular dysfunction, glomerulonephritis, nephropathy, diabetic nephropathy, podocyte dysfunction, podocyte injury, podocytopathies, podocyte foot process effacement, diffuse mesengial sclerosis, congenital nephrotic syndrome, Alpor's syndrome and variants, minimal change disease, focal segmental glomerulosclerosis (FSGS), collapsing glomerulonephropathy, immune and inflammatory glomerulonephropathies, hypertensive nephropathy, and age associated glomerulonephropathy.

8. A method according to claim 7 wherein the kidney disease or condition is selected from the group consisting of nephrotic syndrome, chronic kidney disease, glomerular disease, podocyte dysfunction, and podocyte foot process effacement.

9. A method according to claim 8 wherein the kidney disease or condition is podocyte foot process effacement.

10. A method according to claim 1 wherein the kidney disease or condition comprises podocyte dysfunction characterized by podocyte foot process effacement.

11. A method according to claim 1 comprising treating podocytes with the dynamin ring stabilizer to maintain and/or induce formation of podocyte foot processes.

12. A method according to claim 1 wherein the induction of actin cytoskeleton formation comprises inducing formation of actin stress fibres.

13. A method according to claim 1 comprising administering the dynamin ring stabilizer for inducing focal adhesions and/or formation of actin stress fibres in podocytes.

14. A method for prophylaxis or treatment of podocyte foot process effacement, comprising administering to an individual in need thereof an effective amount of at least one dynamin ring stabilizer, or prodrug or pharmaceutically acceptable salt of the dynamin ring stabilizer.

15. A method according to claim 14 comprising administering to the individual an effective amount of the dynamin ring stabilizer or a pharmaceutically acceptable salt of the dynamin ring stabilizer.

16. A method according to claim 14 wherein the dynamin ring stabiliser is selected from the group consisting of dimeric tyrphostins, iminochromenes, monomeric typhostins, and 3-substituted naphthalene-2-carboxylic acid (benzylidene) hydrazides.

17. A method according to claim 14 wherein the dynamin ring stabiliser is a compound for promoting oligomerization of dynamin into dynamin rings.

* * * * *

UNITED STATES PATENT AND TRADEMARK OFFICE
CERTIFICATE OF CORRECTION

PATENT NO. : 8,809,386 B2  
APPLICATION NO. : 13/321415  
DATED : August 19, 2014  
INVENTOR(S) : Phillip J. Robinson and Sanja Sever Page 1 of 1

It is certified that error appears in the above-identified patent and that said Letters Patent is hereby corrected as shown below:

In the Specification

Column 1, Line 21, please insert the following paragraph:
--GOVERNMENT FUNDING
This invention was made with government support under DK064787 awarded by the National Institutes of Health. The government has certain rights in the invention.--

Signed and Sealed this
Second Day of May, 2023

Katherine Kelly Vidal
*Director of the United States Patent and Trademark Office*

SEQUENCE LISTING

<160> NUMBER OF SEQ ID NOS: 11

<210> SEQ ID NO 1
<211> LENGTH: 46
<212> TYPE: PRT
<213> ORGANISM: Mus musculus

<400> SEQUENCE: 1

Arg Thr Gly Leu Phe Thr Pro Asp Leu Ala Phe Glu Ala Ile Val Lys
1               5                   10                  15

Lys Gln Val Val Lys Leu Lys Glu Pro Cys Leu Lys Cys Val Asp Leu
            20                  25                  30

Val Ile Gln Glu Leu Ile Ser Thr Val Arg Gln Cys Thr Ser
        35                  40                  45

<210> SEQ ID NO 2
<211> LENGTH: 46
<212> TYPE: PRT
<213> ORGANISM: Mus musculus

<400> SEQUENCE: 2

Arg Thr Gly Leu Phe Thr Pro Asp Met Ala Phe Glu Ala Ile Val Lys
1               5                   10                  15

Lys Gln Leu Val Lys Leu Lys Glu Pro Ser Leu Lys Cys Val Asp Leu
            20                  25                  30

Val Val Ser Glu Leu Ala Thr Val Ile Lys Lys Cys Ala Glu
        35                  40                  45

<210> SEQ ID NO 3
<211> LENGTH: 46
<212> TYPE: PRT
<213> ORGANISM: Mus musculus

<400> SEQUENCE: 3

Arg Thr Gly Leu Phe Thr Pro Asp Leu Ala Phe Glu Ala Ile Val Lys
1               5                   10                  15

Lys Gln Val Gln Lys Leu Lys Glu Pro Ser Ile Lys Cys Val Asp Met
            20                  25                  30

Val Val Ser Glu Leu Thr Ser Thr Ile Arg Lys Cys Ser Glu
        35                  40                  45

<210> SEQ ID NO 4
<211> LENGTH: 46
<212> TYPE: PRT
<213> ORGANISM: Mus musculus

<400> SEQUENCE: 4

Arg Thr Gly Leu Phe Thr Pro Asp Met Ala Phe Glu Thr Ile Val Lys
1               5                   10                  15

Lys Gln Val Lys Lys Ile Arg Glu Pro Cys Leu Lys Cys Val Asp Met
            20                  25                  30

Val Ile Ser Glu Leu Ile Ser Thr Val Arg Gln Cys Thr Lys
        35                  40                  45

<210> SEQ ID NO 5
<211> LENGTH: 46
<212> TYPE: PRT
<213> ORGANISM: Drosophila melanogaster

<400> SEQUENCE: 5

Arg Val Gly Leu Phe Thr Pro Asp Met Ala Phe Glu Ala Ile Val Lys
1               5                   10                  15

Arg Gln Ile Ala Leu Leu Lys Glu Pro Val Ile Lys Cys Val Asp Leu
            20                  25                  30

Val Val Gln Glu Leu Ser Val Val Arg Met Cys Thr Ala
        35                  40                  45

<210> SEQ ID NO 6
<211> LENGTH: 46
<212> TYPE: PRT
<213> ORGANISM: Caenorhabditis elegans

<400> SEQUENCE: 6

Arg Val Gly Leu Phe Thr Pro Asp Met Ala Phe Glu Ala Ile Ala Lys
1               5                   10                  15

Lys Gln Ile Thr Arg Leu Lys Glu Pro Ser Leu Lys Cys Val Asp Leu
            20                  25                  30

Val Val Asn Glu Leu Ala Asn Val Ile Arg Gln Cys Ala Asp
        35                  40                  45

<210> SEQ ID NO 7
<211> LENGTH: 46
<212> TYPE: PRT
<213> ORGANISM: Saccharomyces cerevisiae

<400> SEQUENCE: 7

Ala Pro Ser Leu Phe Val Gly Thr Glu Ala Phe Glu Val Leu Val Lys
1               5                   10                  15

Gln Gln Ile Arg Arg Phe Glu Glu Pro Ser Leu Arg Leu Val Thr Leu
            20                  25                  30

Val Phe Asp Glu Leu Val Arg Met Leu Lys Gln Ile Ile Ser
        35                  40                  45

<210> SEQ ID NO 8
<211> LENGTH: 46
<212> TYPE: PRT
<213> ORGANISM: Mus musculus

<400> SEQUENCE: 8

Arg Pro Thr Leu Phe Val Pro Glu Leu Ala Phe Asp Leu Leu Val Lys
1               5                   10                  15

Pro Gln Ile Lys Leu Leu Leu Glu Pro Ser Gln Arg Cys Val Glu Leu
            20                  25                  30

Val Tyr Glu Glu Leu Met Lys Ile Cys His Lys Cys Gly Ser
        35                  40                  45

<210> SEQ ID NO 9
<211> LENGTH: 46
<212> TYPE: PRT
<213> ORGANISM: Mus musculus

<400> SEQUENCE: 9

Arg Thr Gly Leu Phe Thr Pro Asp Leu Ala Phe Glu Ala Ile Val Glu
1               5                   10                  15

Glu Gln Val Val Glu Leu Glu Glu Pro Cys Leu Glu Cys Val Asp Leu
            20                  25                  30

Val Ile Gln Glu Leu Ile Ser Thr Val Arg Gln Cys Thr Ser
        35                  40                  45

<210> SEQ ID NO 10
<211> LENGTH: 46
<212> TYPE: PRT
<213> ORGANISM: Mus musculus

<400> SEQUENCE: 10

Arg Thr Gly Leu Phe Thr Pro Asp Leu Ala Phe Glu Ala Ile Val Ala
1               5                   10                  15

```
Ala Gln Val Val Ala Leu Ala Glu Pro Cys Leu Ala Cys Val Asp Leu
            20                  25                  30

Val Ile Gln Glu Leu Ile Ser Thr Val Arg Gln Cys Thr Ser
            35                  40                  45

<210> SEQ ID NO 11
<211> LENGTH: 46
<212> TYPE: PRT
<213> ORGANISM: Mus musculus

<400> SEQUENCE: 11

Arg Thr Gly Leu Phe Thr Pro Asp Leu Ala Phe Glu Ala Ile Val Lys
1               5                   10                  15

Lys Gln Val Val Lys Leu Lys Lys Pro Cys Leu Lys Cys Val Asp Leu
            20                  25                  30

Val Ile Gln Lys Leu Ile Ser Thr Val Arg Gln Cys Thr Ser
            35                  40                  45
```